US011517576B2

(12) United States Patent
Jung et al.

(10) Patent No.: US 11,517,576 B2
(45) Date of Patent: Dec. 6, 2022

(54) METHODS AND COMPOSITIONS OF BILE ACIDS AND SALTS FOR REDUCTION OF FAT

(71) Applicant: Medytox Inc., Cheongju-si (KR)

(72) Inventors: Hyun Ho Jung, Seoul (KR); Gi Hyeok Yang, Chungcheongnam-do (KR); Junho Lee, Suwon-si (KR); Sujin Cho, Cheongju-si (KR)

(73) Assignee: Medytox Inc., Cheongju-si (KR)

( * ) Notice: Subject to any disclaimer, the term of this patent is extended or adjusted under 35 U.S.C. 154(b) by 0 days.

(21) Appl. No.: 16/908,164

(22) Filed: Jun. 22, 2020

(65) Prior Publication Data
US 2020/0390787 A1 Dec. 17, 2020

Related U.S. Application Data

(62) Division of application No. 15/322,368, filed as application No. PCT/IB2015/001646 on Jun. 26, 2015, now Pat. No. 10,729,700.

(60) Provisional application No. 62/017,891, filed on Jun. 27, 2014.

(51) Int. Cl.
| A61K 31/575 | (2006.01) |
| A61K 45/06 | (2006.01) |
| A61K 9/00 | (2006.01) |
| A61Q 19/06 | (2006.01) |
| A61K 8/63 | (2006.01) |

(52) U.S. Cl.
CPC .............. *A61K 31/575* (2013.01); *A61K 8/63* (2013.01); *A61K 9/0019* (2013.01); *A61K 45/06* (2013.01); *A61Q 19/06* (2013.01); *A61K 2800/74* (2013.01); *A61K 2800/88* (2013.01); *A61K 2800/91* (2013.01)

(58) Field of Classification Search
None
See application file for complete search history.

(56) References Cited

U.S. PATENT DOCUMENTS

| 5,376,646 | A | 12/1994 | Pittrof et al. |
| 5,853,748 | A | 12/1998 | New |
| 7,622,130 | B2 | 11/2009 | Kolodney et al. |
| 7,754,230 | B2 | 7/2010 | Kolodney et al. |
| 7,932,243 | B2 | 4/2011 | Yoo |
| 8,242,294 | B2 | 8/2012 | Moriarty et al. |
| 8,298,556 | B2 | 10/2012 | Kolodney et al. |
| 8,653,058 | B2 | 2/2014 | Hodge et al. |
| 8,846,066 | B2 | 9/2014 | Kolodney et al. |
| 9,272,047 | B2 * | 3/2016 | Seong .................... A61P 31/00 |
| 10,729,700 | B2 * | 8/2020 | Jung .................... A61K 31/575 |
| 2005/0089555 | A1 | 4/2005 | Boderke et al. |
| 2005/0143347 | A1 | 6/2005 | Boderke et al. |
| 2005/0267080 | A1 | 12/2005 | Kolodney et al. |
| 2007/0071706 | A1 | 3/2007 | Zadini et al. |
| 2009/0221528 | A1 | 9/2009 | Denney et al. |
| 2009/0275545 | A1 | 11/2009 | Boderke et al. |
| 2011/0218181 | A1 | 9/2011 | Hodge et al. |
| 2012/0258943 | A1 | 10/2012 | Hodge et al. |
| 2013/0338200 | A1 | 12/2013 | Borsa |
| 2014/0113883 | A1 | 4/2014 | DeLuze |
| 2015/0051182 | A1 | 2/2015 | Kolodney et al. |
| 2016/0339042 | A1 | 11/2016 | Modi |

FOREIGN PATENT DOCUMENTS

| CN | 101357119 A | 2/2009 |
| EP | 2422789 A1 | 2/2012 |
| JP | 2004500378 A | 1/2004 |
| JP | 2007538104 A | 12/2007 |
| JP | 2010536716 A | 12/2010 |
| KR | 1020060117914 A | 11/2006 |
| KR | 1020070110351 A | 11/2007 |
| WO | 2001056547 B1 | 2/2003 |
| WO | 2005112942 A1 | 12/2005 |
| WO | 2008140262 A2 | 11/2008 |
| WO | 2011135020 A1 | 11/2011 |
| WO | 2012131591 A1 | 10/2012 |

OTHER PUBLICATIONS

M. C. Carey, "Bile Acids and Bile Salts: Ionization and Solubility Properties", 1984, HEPATOLOGY, 4(5), pp. 66S-71S. (Year: 1984).*
Hofmann et al., "Bile acid solubility and precipitation in vitro and in vivo: the role of conjugation, pH, and Ca2+ ions", 1992, Journal of Lipid Research, 33(5), pp. 617-626. (Year: 1992).*
Ninomiya et al., "Micelle formation of sodium chenodeoxycholate and solubilization into the micelles: comparison with other unconjugated bile salts," Biochimica et Biophysica Acta, 2003, vol. 1634, pp. 116-125, Elsevier, Amsterdam, Netherlands.
Chinese Office Action dated Sep. 3, 2019 for Chinese Patent Application No. 201580034720.
Gerasimov, "Influence of Sodium and Potassium Ions on Hydrogen Ions Activity in Buffer Solutions", Vestnik Donetskogo Natzional'nogo Universiteta, Ser. A: Prirodnye nauki, vyp, table on p. 180, 2010, Russia.
Hofman et al., "Physicochemical properties of bile acids and their relationship to biological properties: an overview of the problem", J Lipid Research, 1984, vol. 25, pp. 1477-1489, ASBMB, United States.

(Continued)

*Primary Examiner* — My-Chau T. Tran
(74) *Attorney, Agent, or Firm* — Potomac Law Group, PLLC

(57) ABSTRACT

The present invention relates to compositions and methods for treating fat deposit accumulation in a subject. The invention provides a non-surgical method for reducing fat deposits comprising administering an effective amount of a fat-lysing concentration of one or more of cholate and chenodeoxycholate in a pharmaceutically acceptable formulation to the subject in need thereof.

13 Claims, 25 Drawing Sheets

(56) References Cited

OTHER PUBLICATIONS

International Search Report and Written Opinion for PCT/IB2015/001646 dated Feb. 29, 2016.
Kybella, (deoxycholic acid) Label, FDA, Silver Spring, MD (rev. Apr. 2015).
Lapatina, et al., "Mesotherapy in Correction of Local Fat Deposits and Cellulitis", Vestnik Estetitcheskoy Meditsiny, 2009, vol. 8(4), pp. 65-67, Russia.
Office Action for related Russian Patent Application No. 2016149522/15 (079530) dated Jan. 12, 2018.
Rotunda et al., "Lipomas Treated with Subcutaneous Deoxycholate Injections", Journal of the American Academy of Dermatology, 2005, vol. 53, pp. 973-978, United States.
Salti et al., "Phosphatidycholine and Sodium Deoxycholate in the Treatment of Localized Fat: A Double Blind, Randomized Study", Dermatologic Surgery, 2008, vol. 34, pp. 60-66, United States.
Supplementary European Search Report for related European Patent Application No. 15811097.3 dated Jan. 8, 2018.

* cited by examiner

<1.5% CA>

| DCA 1.5% | DCA 1% | DCA 0.5% | CA 1.5% | CA 1% | CA 0.5% | PBS |
|---|---|---|---|---|---|---|
| 3 | 3.9375 | 0.625 | 0.25 | 0 | 0 | 0 |

METHODS AND COMPOSITIONS OF BILE ACIDS AND SALTS FOR REDUCTION OF FAT

BACKGROUND OF THE INVENTION

Liposuction, also known as lipoplasty, liposculpture suction lipectomy or simply lipo, is a cosmetic surgery operation that removes fat from many different sites on the human body. Areas affected can range from the abdomen, thighs and buttocks, to the neck, backs of the arms and elsewhere.

Several factors limit the amount of fat that can be safely removed in one session. There are negative aspects to removing too much fat. Unusual lumpiness and/or dents in the skin can be seen in those patients "over-suctioned". The more fat removed, the higher the surgical risk.

Injection lipolysis is a cosmetic procedure in which drug mixtures are injected into patients with the goal of destroying fat cells. This practice, using drugs generally based on phosphatidylcholine (PPC) and deoxycholate (DCA), evolved from the initial intravenous use of those drug formulations to treat blood disorders.

PPC is a class of phospholipids that incorporate choline as a head group. It is a major component of biological membranes and can be easily obtained from a variety of readily available sources, such as egg yolk or soybeans, from which it is mechanically or chemically extracted using hexane. PPC prevents fatty accumulation and is used to treat liver failure induced by fatty liver, myocardial ischemia, cerebrovascular diseases, and dementia. It has been also recently introduced for lipolysis for obesity treatment in the United States, Europe, and rest of the world.

DCA is one of the secondary bile salts, which are metabolic byproducts of intestinal bacteria. DCA has been used since its discovery in various fields of human medicine and is openly used in lipolysis injections, mixed with PPC. DCA has been used to improve the aqueous solubility of PPC and more recently, medications like amphotericin B, Taxol™, and diazepam. Highly purified PPC can be combined with the DCA, an anti-microbial, benzyl alcohol, and water to form a stable, mixed micelle preparation that can be rapidly sterilized and used for intravenous administration.

In 1966, investigators noted that the intravenous infusion of PPC-containing solutions could remove fat emboli. Later, a drug formulation called Lipostabil® containing 5% PPC and 4.75% DCA was approved in Germany and used in the treatment of fat embolism, dyslipidemia, and alcohol-induced liver cirrhosis.

Among detergents, bile salts are particularly potent solubilizers of lipid bilayer membranes. All biologic cell membranes are composed of the same bi-lipid layer structure, and are therefore subject to solubilization by detergents. Solubilization of cell membranes by a detergent involves distribution of the detergent between lipid bilayers, destabilization of the bilayer, disintegration, and subsequent formation of mixed micelles (composed of detergent and cell membrane lipid). Bile salts, and other detergents, decrease surface tension at the border of immiscible materials and allow the breakdown of large aggregates into smaller and smaller particles. In tissue, these agents dissolve cell membranes and cause cell lysis. An inflammatory response is generated by cell lysis, causing the body to remove the detergent solubilized material.

Recently, Kythera Biopharmaceuticals, a private company located in USA, is developing fat lipolysis injection using PPC free version of DCA. Based on PPC's role as an emulsifier in DCA and its use in the treatment of hyperlipidemia, PPC has been postulated as the active ingredient in lipolysis injection. Detergents, such as DCA, in these prior art compositions were added merely to disperse or solubilize the presumed active ingredient, PPC. However it was demonstrated that the DCA was actually the active agent for localized fat emulsification.

Because DCA is one of the strong detergents in the family of bile salts, treatment of PPC and DCA or DCA alone can evoke unwanted adverse events. Administration of DCA causes the destruction of surrounding tissues from injection sites. The use of DCA for a body fat removal is also associated with significant adverse events including pain, burning sensation, numbness, bruising, edema, swelling, pigmentation, and induration. Moreover, previous researchers suggest an increased risk of breast or colon cancer after DCA exposure.

While meeting with some success, prior techniques and compositions have met with certain limitations. Therefore it would be desirable to have a method of reducing localized fat accumulations that does not require surgery or prolonged recovery time and has fewer adverse side effects than currently available methods. The present invention fulfills this need.

SUMMARY OF THE INVENTION

The invention provides a formulation for the non-surgical removal of a localized fat deposit in a subject. In one embodiment, the formulation comprises a fat-lysing concentration of one or more of cholate and chenodeoxycholate in a pharmaceutically acceptable formulation having a pH of less than 9. In one embodiment, the formulation has a pH of less than 8. In another embodiment, the formulation has a pH of less than 7.5.

In one embodiment, the formulation comprises a fat-lysing concentration of one or more of cholate and chenodeoxycholate at a concentration from about 0.5% to about 4.0%. In another embodiment, the concentration is from about 0.5% to about 2.0%.

In one embodiment, the formulation further comprises at least one additional active ingredient selected from the group consisting of an anti-inflammatory agent, an analgesic, a dispersion agent and a penetration enhancer.

In one embodiment, the formulation further comprises a therapeutic agent selected from the group consisting of an anti-microbial agent, an anti-thrombotic agent, an anti-coagulation agent, a suds-depressant, an anti-inflammatory agent, an anesthetic, an analgesic, a steroid, a tranquilizer, an anti-dispersion agent, and a muscle relaxant.

In one embodiment, the formulation is in an injectable formulation. In another embodiment, the formulation is in a lipolysis injection formulation.

The invention also provides a method for the non-surgical removal of localized fat deposits in a subject having localized fat accumulation. In one embodiment, the method comprises administering a formulation comprising a fat-lysing concentration of one or more of cholate and chenodeoxycholate in a pharmaceutically acceptable formulation having a pH of less than 9.

In one embodiment, the administering step comprises a subcutaneous injection.

In one embodiment, the localized fat accumulation is selected from the group consisting of lower eyelid fat herniation, lipomas, lipodystrophy, and fat deposits associated with cellulite.

In one embodiment, the fat deposit is localized under the eye, under the chin, under the arm, buttock, calf, back, thigh, ankle, or stomach of the subject.

The invention also provides a kit comprising: (a) a first container comprising a formulation for the non-surgical removal of a localized fat deposit in a subject comprising a fat-lysing concentration of one or more of cholate and chenodeoxycholate in a pharmaceutically acceptable formulation having a pH of less than 9; and (b) written instructions for use of the formulation for reducing a fat deposit in a subject without the use of surgery.

In one embodiment, the first container comprises a therapeutic agent selected from the group consisting of: an anti-microbial agent, an anti-thrombotic agent, an anti-coagulation agent, a suds-depressant, an anti-inflammatory agent, an anesthetic, an analgesic, a steroid, a tranquilizer, an anti-dispersion agent, and a muscle relaxant.

In one embodiment, the further comprises a second container wherein the second container comprises a second therapeutic agent selected from the group consisting of: an anti-microbial agent, an anti-thrombotic agent, an anti-coagulation agent, a suds-depressant, an anti-inflammatory agent, an anesthetic, an analgesic, a steroid, a tranquilizer, an anti-dispersion agent, and a muscle relaxant.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1A:
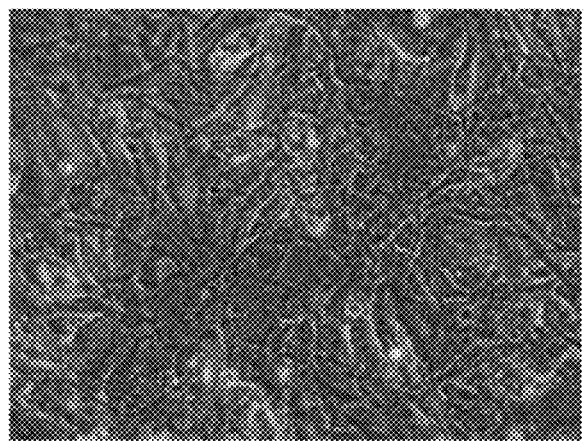
FIGS. 1A, 1B, and 1C are images showing differentiation of 3T3-L1 pre-adipocytes. 3T3-L1 pre-adipocytes (FIG. 1A) were treated with differentiation media (MDI media) and differentiated adipocytes (FIG. 1B) were washed and fixed. After permeation with 0.2% triton-X 100, cells were stained with Oil Red O (FIG. 1C) and photographed at 200× magnification.

The present invention is based on the unexpected discovery that the fat lysing effect of cholate in vivo was not predictable based on the activities of cholate observed in vitro and ex vivo. That is, although cholate exhibited relatively low lytic activity compared with deoxycholate and chenodeoxycholate in vitro, cholate exhibited superior results in vivo. For example, treatment of cholate in vivo caused significantly reduced adverse events in the skin compared to the treatment of deoxycholate. This unexpected fat lysing effect of cholate having reduced adverse events in vivo supports the use of cholate as an active component in lipolysis injection, particularly at a concentration that was not predicted from the in vitro and ex vivo results.

The present invention addresses the problem of localized fat accumulation in animals by providing a non-surgical method for reducing fat deposits. In one embodiment, the invention comprises administering an effective amount of a fat-lysing concentration of one or more of cholate and chenodeoxycholate in a pharmaceutically acceptable formulation.

The invention relates to the use of a bile acid or salt thereof to reduce fat in an animal, preferably a mammal, more preferably a human. In one embodiment, the bile acid or salt thereof is one or more of cholate and chenodeoxycholate.

In one embodiment, the present invention relates to the use of one or more of cholate and chenodeoxycholate to reduce subcutaneous fat accumulations in a mammal by administering a pharmaceutically acceptable formulation locally to a target site. In one embodiment, the formulation is in the form of a lipolysis injection.

This invention relates to a method of reducing a fat deposit in a mammal comprising contacting the fat deposit with a formulation comprising one or more of cholate and chenodeoxycholate.

In another embodiment, the invention relates to a method of treating cellulite and extra fat deposits with one or more of cholate and chenodeoxycholate in order to lyse adipose cells associated with the cellulite and extra fat deposits.

In another embodiment, the invention relates to a method of fat removal by controlling the pH of the formulation to improve the activity of one or more of cholate and chenodeoxycholate. In one embodiment, the formulation comprising one or more of cholate and chenodeoxycholate can be formulated to have a suitable pH of less than about 9.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About," as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

The term "bile acid," as used herein, includes steroid acids (and/or the carboxylate anion thereof), and salts thereof, found in the bile of an animal (e.g., a human), including, by way of non-limiting example, cholic acid, cholate, deoxycholic acid, deoxycholate, hyodeoxycholic acid, hyodeoxycholate, glycocholic acid, glycocholate, taurocholic acid, taurocholate, chenodeoxycholic acid, chenodeoxycholate, lithocholic acid, lithocolate, and the like (and salts thereof).

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "composition" or "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Local administration" means administration of a pharmaceutical agent to or to the vicinity of a muscle or a subdermal location in a patient by a non-systemic route. Thus, local administration excludes systemic routes of administration, such as intravenous or oral administration.

"Peripheral administration" means administration to a location away from a symptomatic location, as opposed to a local administration.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

A "therapeutic" treatment is a treatment administered to a subject who exhibits signs or symptoms of pathology, for the purpose of diminishing or eliminating those signs or symptoms.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacology.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Stability and activity of bile salts are largely affected by their pH condition. The present invention is partly related to the observation that the safety of bile salt injection is improved by adjustment of pH condition.

The invention relates to the discovery that the combination of the appropriate concentration range of a bile salt in a proper pH range is important in achieving a desirable therapeutic result by reducing adverse events. For example, a lower concentration of a bile salt can be used in a lower pH formulation because the lower pH condition enhances the cell lysis activity of the bile salt. Preferably, the lower pH used does not increase the adverse effects of the bile salt formulation. Accordingly, adverse effects can be distinguished from the cell lytic activity in a proper pH condition. Therefore, in some instances, the use of a lower concentration of a bile salt in a lower pH formulation can reduce the adverse effects without reduction of cell lytic activity of the bile salt.

In the case of deoxycholate, precipitation of deoxycholate was observed in lower pH solutions. As a result, higher pH buffers are required for deoxycholate. However, pH solutions that are higher than physiological exhibits adverse events. Accordingly, the invention provides a formulation of one or more of cholate and chenodeoxycholate solution of physiological pH and low concentrations that provides additional advantages such as reduction of adverse events compared to a formulation of deoxycholate.

The invention is based on the unexpected fat lysing effect of cholate in vivo whereby cholate does not exhibit adverse effects to the recipient at a concentration that otherwise deoxycholate exhibits adverse effects. Accordingly, the invention provides a formulation of cholate whereby the concentration of cholate can be higher than the concentration of deoxycholate, yet exhibits a reduced adverse effect in the patient. In another aspect, the invention provides a formulation of cholate whereby the concentration of cholate can be the same as the concentration of deoxycholate, but results in a more fat lysing effect yet exhibits a reduced adverse effect in the patient. Therefore, the invention provides a safer lipolysis injection comprising cholate at an effective concentration that does not exhibit adverse effects compared to using deoxycholate.

In one embodiment, the invention provides compositions and methods for using one or more of cholate and chenodeoxycholate as an active component for fat reduction in a mammal. In one embodiment, the invention provides compositions and methods for using one or more of cholate and chenodeoxycholate in a lipolysis injection.

In one embodiment, the invention provides compositions and methods useful in the non-surgical reduction of localized fat deposits in patients in need thereof whereby the method comprises using a composition comprising a pharmacologically active bile acid or salt therefore, for example cholate and chenodeoxycholate. The composition of the invention can additionally include other agents such as anti-inflammatory agents, analgesics, dispersion agents and pharmaceutically acceptable excipients. The compositions of the invention are useful for treating localized accumulations of fat including fat deposits under the eye, chin, or arm, as well as the buttock, calf, back, thigh, ankle, or stomach of a mammal. In another embodiment, the methods may reduce specific types of fat deposits such as, for example, eyelid fat herniation, lipomas, lipodystrophy, buffalo hump lipodystrophy, or fat deposits associated with cellulite. In one embodiment, the fat reduction does not require surgical procedures such as liposuction.

In one embodiment, the compositions of the invention are formulated to be suitable for injection directly into a treatment site of a patient in need of fat reduction without the need for surgical intervention.

In one embodiment, a non-surgical method of fat removal does not include liposuction, lipoplasty or suction lipectomy.

In one embodiment, the present invention provides compositions, methods, and kits for reducing subcutaneous fat deposits as well as tightening loose skin.

Composition

The invention provides a composition useful in the non-surgical reduction or removal of localized fat deposits in patients in need thereof. In one embodiment, the composition comprises an effective fat lysing amount of one or more of cholate and chenodeoxycholate. In one embodiment, the compositions of the invention are useful for treating among other things localized accumulations of fat including lower eyelid fat herniation, lipodystrophy and fat deposits associated with cellulite. Preferably, the compositions of the invention are used so as to not require surgical procedures such as liposuction.

In one embodiment, the invention provides a composition of biologically compatible bile acids or salts thereof including one or more pharmacologically active bile acid and salt thereof and pharmaceutically acceptable excipients in an aqueous vehicle. In particular, it is within the scope of the present invention that pharmacologically active bile acid or salt thereof is used to lyse fat.

Several bile acids and salts thereof are included in the invention. For example, the bile acids and salts thereof encompassed in the invention are selected from cholic acid, chenodeoxycholic acid, and any salt thereof. In various aspects, any bile acid or bile acid conjugate may be in the form of a physiologically acceptable salt, e.g., the sodium salt or a conjugate with taurine or glycine of cholic acid or chenodeoxycholic acid. In one aspect, the term cholic acid refers to the sodium salt of cholic acid. In one embodiment, cholic acid (cholate) is the active ingredient in the formulation of the invention. In another aspect, the term chenodeoxycholic acid refers to the sodium salt of chenodeoxycholic acid. In one embodiment, chenodeoxycholic acid (chenodeoxycholate) is the active ingredient in the formulation of the invention.

In some instances, the terms cholate compound, cholate and cholic acid are used interchangeably. In some instances, the terms chenodeoxycholate compound, chenodeoxycholate and chenodeoxycholic acid are used interchangeably.

In one embodiment, adequate quantities of suitable bile acid as a defined pharmaceutical composition is herein provided. In one aspect, particular cholate and chenodeoxycholate pharmaceutical compositions are free of all moieties of animal origin and of mammalian and/or bacterial pyrogens. In another aspect, adequate quantities of suitable one or more of cholate and chenodeoxycholate as defined pharmaceutical compositions are provided which can be used as an injectable pharmaceutical composition for localized fat removal, along with related composition. The defined one or more of cholate and chenodeoxycholate injectates of the present invention may be combined with a molecule that causes fat to die.

In some embodiments, the bile salt includes a cation selected from the group consisting of sodium ($Na^+$), potassium ($K^+$), lithium ($Li^+$), magnesium ($Mg^{2+}$), calcium ($Ca^{2+}$), barium ($Ba^{2+}$), strontium ($Sr^{2+}$), and ammonium ($NH_4^+$). In some embodiments, the detergent comprises a bile salt with a cation that is an alkali metal or an alkaline earth metal. Preferably, the alkali metal is sodium ($Na^+$), potassium ($K^+$), or lithium ($Li^+$) and the alkaline earth metal is magnesium ($Mg^{2+}$), calcium ($Ca^{2+}$), barium ($Ba^{2+}$), or strontium ($Sr^{2+}$). In certain embodiments, bile salts used in the methods and compositions described herein are pharmaceutically acceptable salts including, by way of non-limiting example, the sodium and potassium salts thereof.

In certain embodiments, the concentration of one or more of cholate and chenodeoxycholate compositions of the invention may comprise about 0.5%, about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, or any range derivable therein, of the present compositions by weight or volume. Thus, it is contemplated that the one or more of cholate and chenodeoxycholate compositions may comprise one or more of cholate and chenodeoxycholate in any combination or percentage range.

In one embodiment, the compositions of the invention herein are in a solution. Preferably the solution is aqueous.

In one embodiment, the present invention relates to a solution for subcutaneous injection comprising: (i) a therapeutically effective amount of one or more pharmacologically active cholate and chenodeoxycholate; and (ii) a pharmaceutical, veterinary, or cosmetic excipient.

In some embodiments, the solution can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents.

In some embodiments, a solution is in a container that contains up to 500 mL of solution. Such container can be a syringe or syringe-loadable container.

The compositions (e.g., solutions) include a therapeutically effective amount of one or more of cholate and chenodeoxycholate. Such therapeutically effective amounts are effective to reduce a subcutaneous fat deposit or tighten a region of loose skin with adverse effects.

One or more of cholate and chenodeoxycholate in a solution of the invention can be at a concentration of about 0.001 to 10, 0.01 to 5, or 0.1 to 2% w/w, w/v, or v/v. Preferably, one or more of cholate and chenodeoxycholate in the solution can be at a concentration of about 0.1-5 w/w or more preferably about 1% w/w.

In one embodiment, one or more of cholate and chenodeoxycholate is formulated to be at a pH of lower than about 9 in order for the one or more of cholate and chenodeoxycholate to be effective in lysing fat. In one embodiment, one or more of cholate and chenodeoxycholate is formulated to be at a pH of lower than about 8 in order for the one or more of cholate and chenodeoxycholate to be effective in lysing fat. In one embodiment, one or more of cholate and chenodeoxycholate is formulated to be at a pH of lower than about 7.5 in order for the one or more of cholate and chenodeoxycholate to be effective in lysing fat. In one embodiment, one or more of cholate and chenodeoxycholate is formulated to be at a pH of lower than about 7.0 in order for the one or more of cholate and chenodeoxycholate to be effective in lysing fat. Preferably, the formulation is a liquid formulation where one or more of cholate and chenodeoxycholate is in a stable form at 25° C. As used herein, a stable form is not a gelation form or a precipitation form.

In one embodiment, one or more of cholate and chenodeoxycholate is formulated to be at a concentration of about 0.5% to about 4.0%. In one embodiment, one or more of cholate and chenodeoxycholate is formulated to be at a concentration of about 0.5% to about 2.0%. Preferably, the formulation is a liquid formulation where one or more of cholate and chenodeoxycholate is in a stable form at 25° C. As used herein, a stable form is not a gelation form or a precipitation form.

In one embodiment, one or more of cholate and chenodeoxycholate is formulated to be at a concentration of about 0.5% to about 4.0% in a pH buffer of less than about 9. In one embodiment, one or more of cholate and chenodeoxycholate is formulated to be at a concentration of about 0.5% to about 4.0% in a pH buffer of less than about 8. In one embodiment, one or more of cholate and chenodeoxycholate is formulated to be at a concentration of about 0.5% to about 4.0% in a pH buffer of less than about 7.5. In one embodiment, one or more of cholate and chenodeoxycholate is formulated to be at a concentration of about 0.5% to about 4.0% in a pH buffer of less than about 7. Preferably, the formulation is a liquid formulation where one or more of cholate and chenodeoxycholate is in a stable form at 25° C. As used herein, a stable form is not a gelation form or a precipitation form.

In one embodiment, one or more of cholate and chenodeoxycholate is formulated to be at a concentration of about 0.5% to about 2.0% in a pH buffer of less than about 9. In one embodiment, one or more of cholate and chenodeoxycholate is formulated to be at a concentration of about 0.5% to about 2.0% in a pH buffer of less than about 8. In one embodiment, one or more of cholate and chenodeoxycholate is formulated to be at a concentration of about 0.5% to about 2.0% in a pH buffer of less than about 7.5. In one embodiment, one or more of cholate and chenodeoxycholate is formulated to be at a concentration of about 0.5% to about 2.0% in a pH buffer of less than about 7. Preferably, the formulation is a liquid formulation where one or more of cholate and chenodeoxycholate is in a stable form at 25° C. As used herein, a stable form is not a gelation form or a precipitation form.

In one embodiment, the invention provides a formulation of one or more of cholate and chenodeoxycholate at a concentration of about 0.5% to about 2.0% at a pH buffer of less than about 8 in a stable form at 25° C. An advantage of the formulation of the invention is that the bile salt solution of physiological pH and low concentration reduces adverse events when using a higher pH solution and higher bile salt concentrations.

Method

The composition of the invention can be applicable to numerous clinical situations. The present invention relates to the use of one or more pharmacologically active one or more of cholate and chenodeoxycholate to reduce subcutaneous fat accumulations in a mammal by administering such formulation locally to a target site. Other uses for this composition may include dissolving lipomas, fat, mesotherapy, separating tissue, tumor reduction, cancer reduction, cancer treatment, and any other clinical situation where one might want to use loosen, remove, assist the body consumption or resolution of wax, lipids, proteins, or carbohydrates from a part or region of the body. For example, in the treatment of lipomas, the composition can be injected injected subcutaneously in contact with the lipomas to lyse the lipomas. Any other suitable method of application to the lipomas can also be used.

In one embodiment, the compositions of the invention is used to reduce a fat deposit in a subject. In some instances, fat deposit is associated with a condition selected from the group consisting of obesity, fat redistribution syndrome, eyelid fat herniation, lipomas, Dercum's disease, lipodystrophy, buffalo hump lipodystrophy, dorsocervical fat, visceral adiposity, breast enlargement, hyperadiposity, diffused body fat around trunk and arms, and fat deposits associated with cellulite. In a preferred embodiment, the methods of the invention do not include performing surgery on the subject.

The composition of the invention may be useful in the treatment of granulomas, scars, tumors, acne cysts, sebaceous cysts, sebaceous hyperplasia, diseases of the sebum, acne related dermatoses, diseases of the subcutaneous fat, tumors, tattoo removal, infections and biofilms, cellulite, fatty deposits, fat tissue, and related conditions. It could also be used to even out skin contour defects (such as breast asymmetry, or lip assymmetry, for example, after over correction with a skin filler, or a hyperresponse of the body to an injection). Such a procedure could be done in living tissue, tissue removed from the body, or for assistance in pathological or detective assessments. It could be done on tissue, serum, or any other body partition. In addition to human care, the composition is also applicable to animal care.

In one embodiment, the present invention relates to methods for reducing fat in a subject. Such methods comprise the step of: administering locally to a target region a composition of the invention.

In some embodiments, the administering step involves delivering the compositions of the invention via a subcutaneous or transdermal injection.

In some embodiments, the administering step involves delivering the compositions of the invention via a dermal patch, a pump, or subdermal depot.

In some embodiments, the administering step involves delivering the compositions of the invention topically or subcutaneously.

In some embodiments, the region of target site being treated is under eye, under chin, under arm, buttock, cheek, brow, calf, back, thigh, ankle, or stomach.

In some embodiments, the compositions used for reducing fat in a subject are formulated with a skin tightening solution. Such skin tightening solution can further comprise a second therapeutic agent selected from the group consisting of: anti-microbial agents, vasoconstrictors, anti-thrombotic agents, anti-coagulation agents, suds-depressants, anti-inflammatory agents, analgesics, dispersion agents, anti-dispersion agents, penetration enhancers, steroids, tranquilizers, muscle relaxants, and anti-diarrhea agents.

In some embodiments, the methods of the invention do not include performing surgery on the subject.

In certain embodiments, the time between the first treatment and second treatment of the invention is at least one week, at least two weeks, at least one month, at least 2 months, at least 12 weeks, at least 13 weeks, at least 14 weeks, at least 15 weeks, at least 16 weeks, at least 17 weeks, at least 18 weeks, at least 19 weeks, at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, at least 39 weeks, at least 40 weeks, at least 41 weeks, at least 42 weeks, at least 43 weeks, at least 44 weeks, at least 45 weeks, at least 46 weeks, at least 47 weeks, at least 48 weeks, at least 49 weeks, at least 50 weeks, at least 51 weeks, at least 52 weeks or more.

Pharmaceutical Compositions

In one embodiment, the invention provides a liquid pharmaceutical composition comprising one or more of cholate and chenodeoxycholate in a pH buffer of less than about 9, less than about 8, less than about 7.5, or less than about 7. In one embodiment, one or more of cholate and chenodeoxycholate is stable in the liquid pharmaceutical composition at 25° C. In one embodiment, being stable in the liquid pharmaceutical composition at 25° C. means that one or more of cholate and chenodeoxycholate is not in a gelation form or precipitation form.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Controlled- or sustained-release formulations of a pharmaceutical composition of the invention may be made using conventional technology.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Bile Acids and Salts for Reduction of Fat

The results presented herein demonstrate the unexpected finding that fat lysing effect of cholate enables the use of cholate as an active component of lipolysis injection, particularly at a concentration that was not predicted from the in vitro and ex vivo results.

The materials and methods employed in these experiments are now described.

Cell Culture and Adipocyte Differentiation In Vitro

3T3-L1 cells were cultured in Dulbecco's modified Eagle's media (DMEM) supplemented with 10% fetal bovine serum in humidified atmosphere of 5% $CO_2$/95% air at 37° C. to confluence. To induce adipocyte differentiation, 3T3-L1 pre-adipocytes were seeded in 96-well plate (5×10$^3$ cells/well) and grown until 2 days post-confluence (day 0) and then treated for 2 days with growth media plus MDI (0.5 µM methylisobutylxanthine, 1 µM dexamethasone and 10 ug/ml insulin; all from Sigma-Aldrich Chemical, St. Louis, Mo., USA), followed by 2 days of treatment with the media containing 10 ug/ml insulin alone. Medium was replaced every 2 days for the following 8 days.

Oil Red O staining

Seven to ten days after the induction of differentiation, cells were rinsed twice with phosphate buffered saline (PBS), fixed with 10% formalin for 1 hour, and washed three times with PBS. Cells were stained with filtered Oil Red O (0.3%) working solution for 20 minutes and stained cells were washed three times with distilled water. Images were collected using an Olympus inverted microscope equipped with an Olympus digital camera.

Cell Lysis Effect by Detergent In Vitro

Differentiated adipocytes in 96 well plate were washed twice with PBS and incubated in various concentrations of bile salts in serum free DMEM. After 1 hour incubation at 37° C., media were changed and 20 µl of MTT solution (5 mg MTT/ml in PBS) was added into each well and incubated for 1 hour at 37° C. The resultant formazan product was dissolved in 100 µl of DMSO/well and cell viability was determined by measuring the optical density at 570 nm ($OD_{570}$) using a microplate reader.

Preparation of Adipose Tissues from Mice and Ex Vivo Fat Lysis Assay

Inguinal fat (subcutaneous fat) pads were excised from diet induced obese mice and chopped to about the same size. 100 mg tissue samples were transferred to 48 well plates and incubated with 350 µl of various concentrations and pH of DCA, CDCA, CA, and phosphate buffer for 10 minutes. 70 µl of MTT solution (5 mg/ml in PBS) was added into each well and incubated for overnight at 37° C. The solution was removed and precipitated formazan product was dissolved in 300 µl of DMSO. Tissue viability was monitored by measuring the optical density at 570 nm ($OD_{570}$) using a microplate reader.

Induction of Diet Induced Obesity in Mice

Four week old male C57BL/6N mice were purchased from Orient Bio (Sungnam, Korea). Mice were fed a high fat diet (D12331-consisting 58% of calories from fat, 16.4% of calories from protein and 25.5% of calories from carbohydrate, primarily sucrose; Research Diets, New Brunswick, N.J., USA) beginning at 4 weeks of age to 18 weeks. Mice were housed in a climate controlled environment (22.8±2.0° C., 45~50% humidity) with a 12 hour light/12 hour dark cycle. Water and designated diet were available ad libitum. Body weight of individual mouse was monitored every other week.

In Vivo Monitoring of Bile Salts Induced Fat Loss

Male C57BL/6N mice were caged and fed a high fat diet during 12 weeks. In vivo effects of bile salts were monitored by direct injection of bile salt to the subcutaneous fat tissue. Briefly, after the induction of diet induced obesity, mice were anesthetized with ketamine and xylazine (60 mg/kg and 12.5 mg/kg, respectively; administered by intraperitoneal injection). The injection sites of mice were shaved with an electronic clipper. 100 µl of Bile salts (DCA, CDCA, and CA, 1% w/v) was injected into the right inguinal fat pad of obese mouse. Injections were repeated 4 more times during 2 weeks. The left inguinal fat pads of mice were received with same volume of PBS as a control. Mice were sacrificed at 4 days after the final injection. The body weight and inguinal fat pad weight of each group of mice were measured. Fat tissues of injected region were dissected, fixed with 10% formalin, and embedded into a paraffin block for histologic examination.

Quantitation of In Vivo Necrotic Area

After the induction of diet induced obesity, mice were anesthetized with ketamine and xylazine (60 mg/kg and 12.5 mg/kg, respectively; administered by intraperitoneal injection). The injection sites of mice were shaved with an electronic clipper. Various concentrations of bile salts (DCA, CDCA, and CA) solutions in 100 μl volume of PBS were injected to the inguinal fat pads of obese mice. Mice were sacrificed at 1 day after the injection. Mouse inguinal fat pads were stained with 2% TTC (Sigma-Aldrich Chemical, St. Louis, Mo., USA) in PBS for 2 hour to identify the non-necrotic and necrotic areas and subsequently immersed in 10% formalin to enhance the contrast. The necrotic area was displayed as the area unstained by TTC. The appearance and area of necrotic fat regions were captured and imaged by scanner. The necrotic area of fat pad treated DCA, CDCA, CA, and PBS was calculated by Image J.

Stability of Bile Salts in Aqueous Solution

To test the solubility and stability of bile salts, various pH of phosphate buffer (10 mM; pH 6.5, 6.7, 7.0, 7.2, 7.4, 7.6, 7.8, 8.0, 8.3) were prepared by dissolving dibasic sodium phosphate and monobasic sodium phosphate in water. 0.01 g of bile salts (UDCA, DCA, CDCA and CA) were dissolved in 1 ml of phosphate buffer and placed at room temperature for 10 days.

In vivo monitoring of tissue specific effects of bile salts 100 μl of DCA and CA (1%, 0.5% and 0.25%), and PBS was injected into the tails (1 cm caudal to its base) of female ICR mice. Mice were sacrificed 14 days later, at which time tissue at the injection site was harvested and fixed in 4% formalin. Standard histological sections were cut perpendicular to the long axis of the tail within 5 mm of the injection site. Samples were then prepared for staining with Hematoxylin and Eosin (H & E). Images were captured by an Olympus microscope equipped with an Olympus digital camera.

In Vivo Monitoring of Adverse Events on the Skin

To monitor adverse effects of bile salts on the skin, various concentrations (1.5%, 1% and 0.5% in 100 μl volume) of DCA, CA and PBS were injected in the plank of mice subcutaneously. Injections were repeated 1 more times 3 days after first injection. Mice were sacrificed at 4 days after the final injection. The severity of skin lesion was assessed using the following criteria. The total skin severity score was defined as the sum of the individual scores for each of the following character and length of lesion. Length of lesion is determined by measuring the longest diameter of the largest lesion identified. Measured length should involve the lesion only and not cross over clinically normal skin. The length of lesion involvement within each injected site was scored from 0 to 3, where 0=no involvement; 1=≤0.2 cm, 2=0.2~0.5 cm, 3=>0.5 cm of the length of site affected. The character of lesion was scored from 0 to 3, where 0=no lesion present, 1=excoriation only one or one, small punctate crust (<2 mm), 2=multiple, small punctate crusts or coalescing crust (≥2 mm), 3=erosion or ulceration.

Bile Salt-Induced Paw Edema

Male SD rats (6 weeks old) were purchased from Koatech Co. (Seoul, Korea) and used after 1 week of acclimation. Rats (200~230 g) were randomly selected and the volume of intact rats paw was measured in all groups using a digital caliper (Bluebird, Seoul, Korea). Before inducing the paw edema, the rats were anesthetized with ketamine and xylazine (60 mg/kg and 12.5 mg/kg, respectively; administered by intraperitoneal injection). To induce the edema, rats received 100 μl of various bile salts and PBS into the plantar region of the hind foot of rats. Measurements of the paw volume were performed by a caliper immediately before the bile salts injection and 4 hours after injection.

The results of the experiments are now described.

Biological Activity of Bile Acids and Salts

The biological activity of a bile salt molecule is tightly linked to its chemical properties, such as the number and orientation of hydroxyl groups or its conjugation. These parameters directly affect its hydrophobicity, which is a well-known predictor of toxicity and detergent strength. The hydrophilic index of bile salts is not only proportional to the number of hydroxyl groups but is also influenced by their position on both sides of the sterol ring.

The detergent power of bile salts directly influences their toxicities. Generally, more potent detergent show more toxic properties. DCA is often used as a biological detergent to lyse cells and solubilize cellular components because DCA is known to be one of the strongest detergents in the family of bile salts. The use of DCA for a body fat removal is associated with significant adverse events. To avoid severe side effects, use of more safe bile salts to replace DCA is desirable. However, it is expected that less toxic bile salts also would have weak detergent power and biological activities.

Figure 1B:
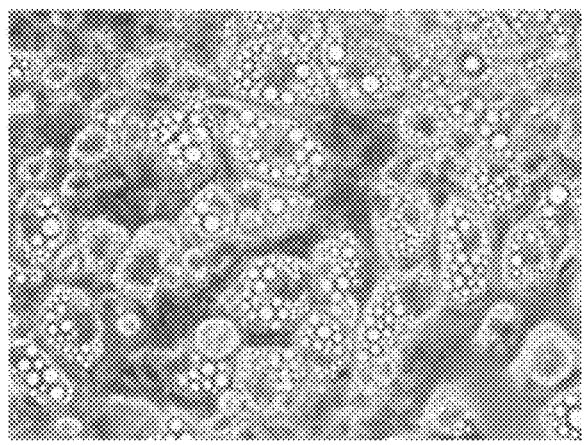
Figure 1C:
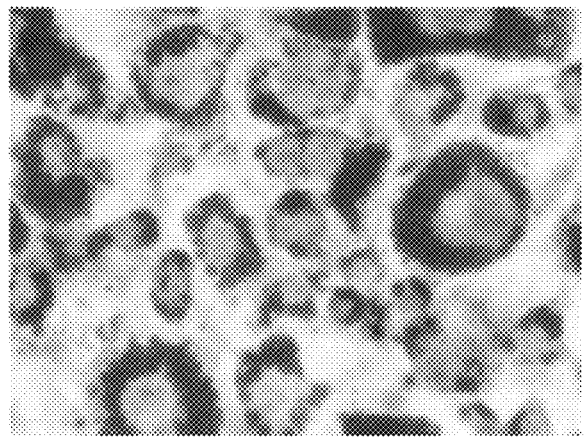
Figure 2A:
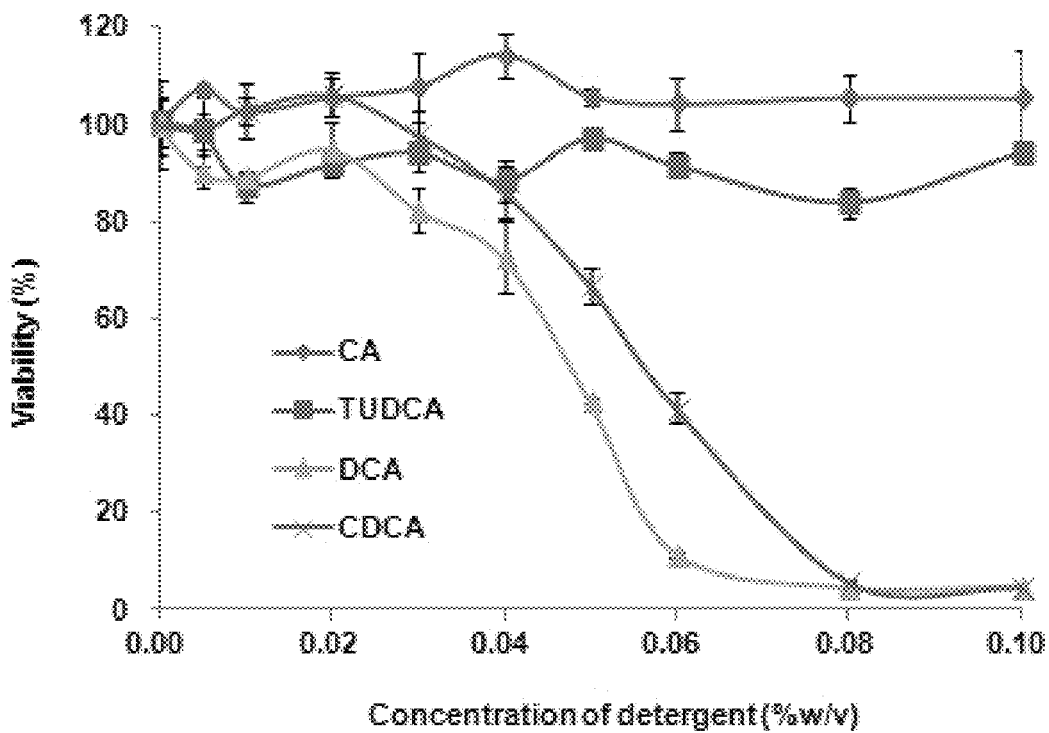
FIGS. 2A, 2B, and 2C are images showing cell lysis effects of detergents in 3T3-L1 adipocytes. Differentiated 3T3-L1 adipocytes were exposed to deoxycholate (DCA), chenodeoxycholate (CDCA), taurourosodeoxycholate (TUDCA), and cholate (CA) (0~0.1%) (FIG. 2A), and TUDCA and CA (0~2%) (FIG. 2B), and ursodeoxycholate (UDCA), hyodeoxycholate (HDCA), and CA (0~1%) (FIG. 2C) for 1 hour and cell viability was measured by 3-(4,5-dimethylthiazol-2-yl)-2,5-diphenyltetrazolium bromide (MTT) assay. All detergents except TUDCA show dose-dependent cell lysis effects. The experiment was performed on three replicates for each treatment. Results are expressed as total percentage of viable cell as compared with untreated control.
Figure 2B:
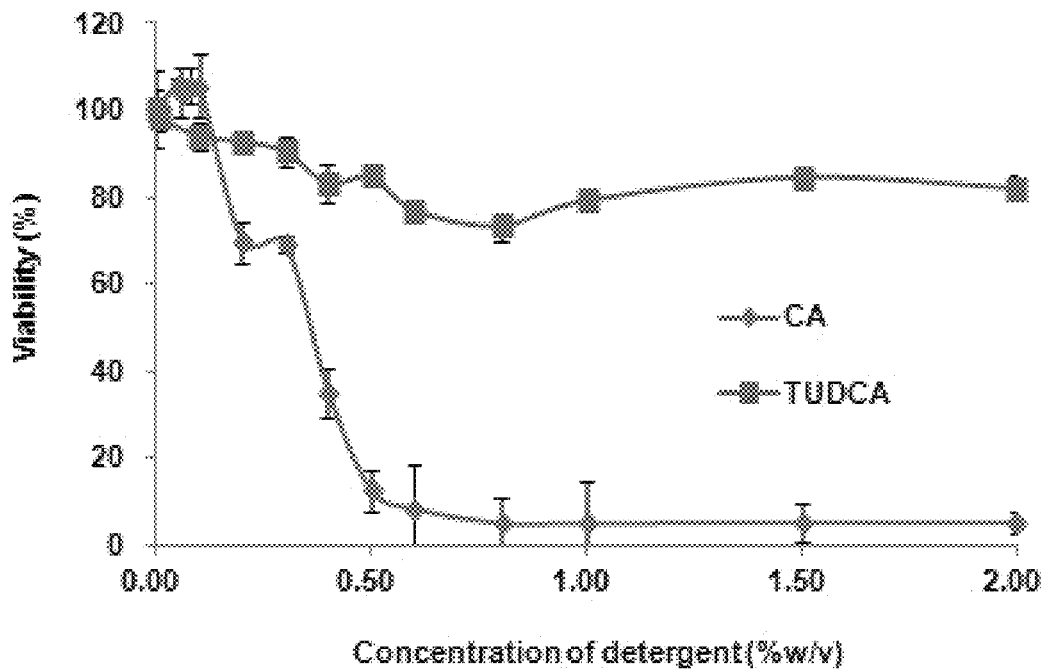
Figure 2C:
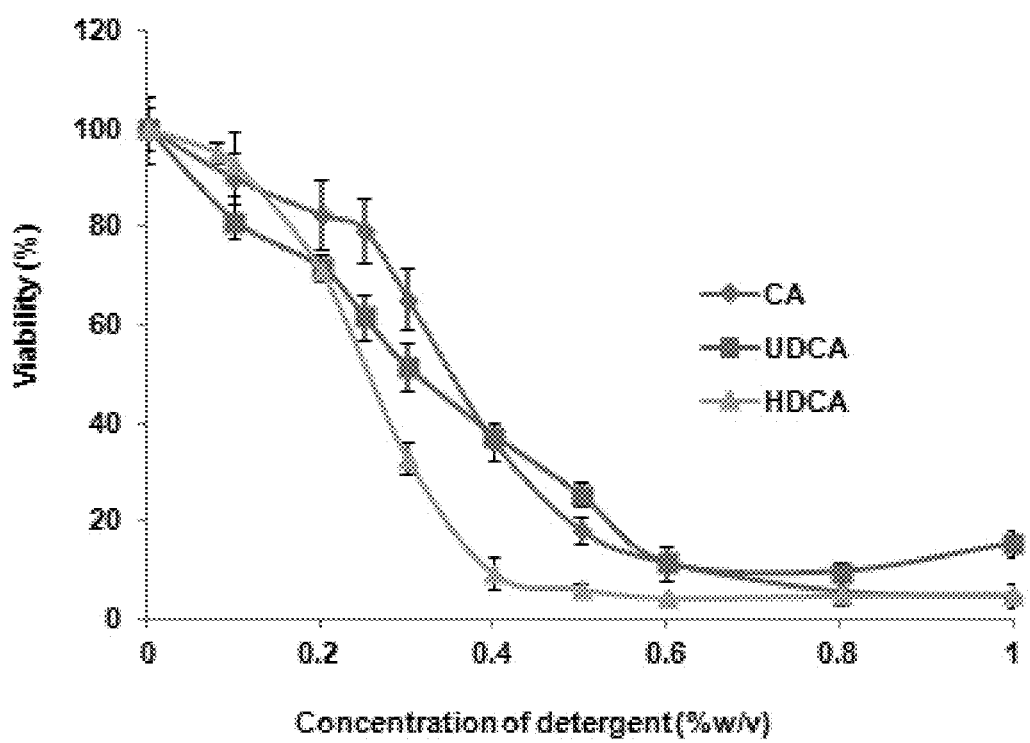

For this reason, experiments were conducted to compare cell lysis activity of various bile salts compared to the effects of DCA using a simple, quantitative assay measuring cell viability. To monitor the adipocyte lysis activity, a differentiated 3T3-L1 adipocyte cell line was used (FIGS. 1A, 1B, and 1C). Cell viability was monitored using an MTT assay. In preliminary experiments, the cell lysis effect of bile salts including TUDCA, CDCA, CA, HDCA, UDCA and DCA were compared in various concentrations. In low concentration (e.g., below 0.1%), only two types of bile salts, DCA, CDCA reduced the viability of adipocyte cells (FIG. 2A). CDCA showed similar cell lysis activity to DCA at similar concentrations. To test the lysis effect of the remaining bile salts in high concentration, experiments were performed using up to 2% concentration of CA and TUDCA. Treatment of TUDCA did not reduce the viability of adipocyte cells. However, CA showed cell killing in these higher concentrations (FIG. 2B). HDCA and HDCA showed slightly higher cell killing effect compared to CA in similar concentration (FIG. 2C). The cell lysis activity of CA, HDCA and UDCA was greatly lower than DCA and CDCA. To compare the relative cell lysis activity of each bile salt, the $EC_{50}$ (concentration that kills 50% of the cells) of DCA, CDCA, HDCA, UDCA and CA was measured. The $EC_{50}$ of DCA, CDCA, HDCA, UDCA and CA was 0.051%, 0.060%, 0.42%, 0.25% and 0.42%, respectively (Table 1). The $EC_{50}$ of CA was about 7~8 fold higher than DCA and CDCA.

TABLE 1

The EC50 values of bile salts required to lysis of adipose cells in vitro.

| Detergent | ED50 (% w/v) |
| --- | --- |
| Deoxycholate (DCA) | 0.0509 |
| Chenodeoxycholate (CDCA) | 0.0597 |
| Cholate (CA) | 0.42 |
| Hyodeoxycholate (HDCA) | 0.249 |
| Ursodeoxycholate (UDCA) | 0.328 |

Results from the in vitro conditions suggested that DCA and CDCA can effectively lyse adipose cells and therefore are considered as components of lipolysis injection. Without wishing to be bound by any particular theory, no cell lysis effect of TUDCA may be due to its low detergent activity, suggesting that TUDCA is not suitable for lipolysis injection. The very low lytic activity of CA, HDCA and UDCA in in vitro conditions, suggest that very high concentration of CA, HDCA and UDCA may be required as a component of lipolysis injection. Therefore, it is believed that only CDCA can effectively substitute for DCA in lipolysis injection from the in vitro results presented herein.

Figure 3A:
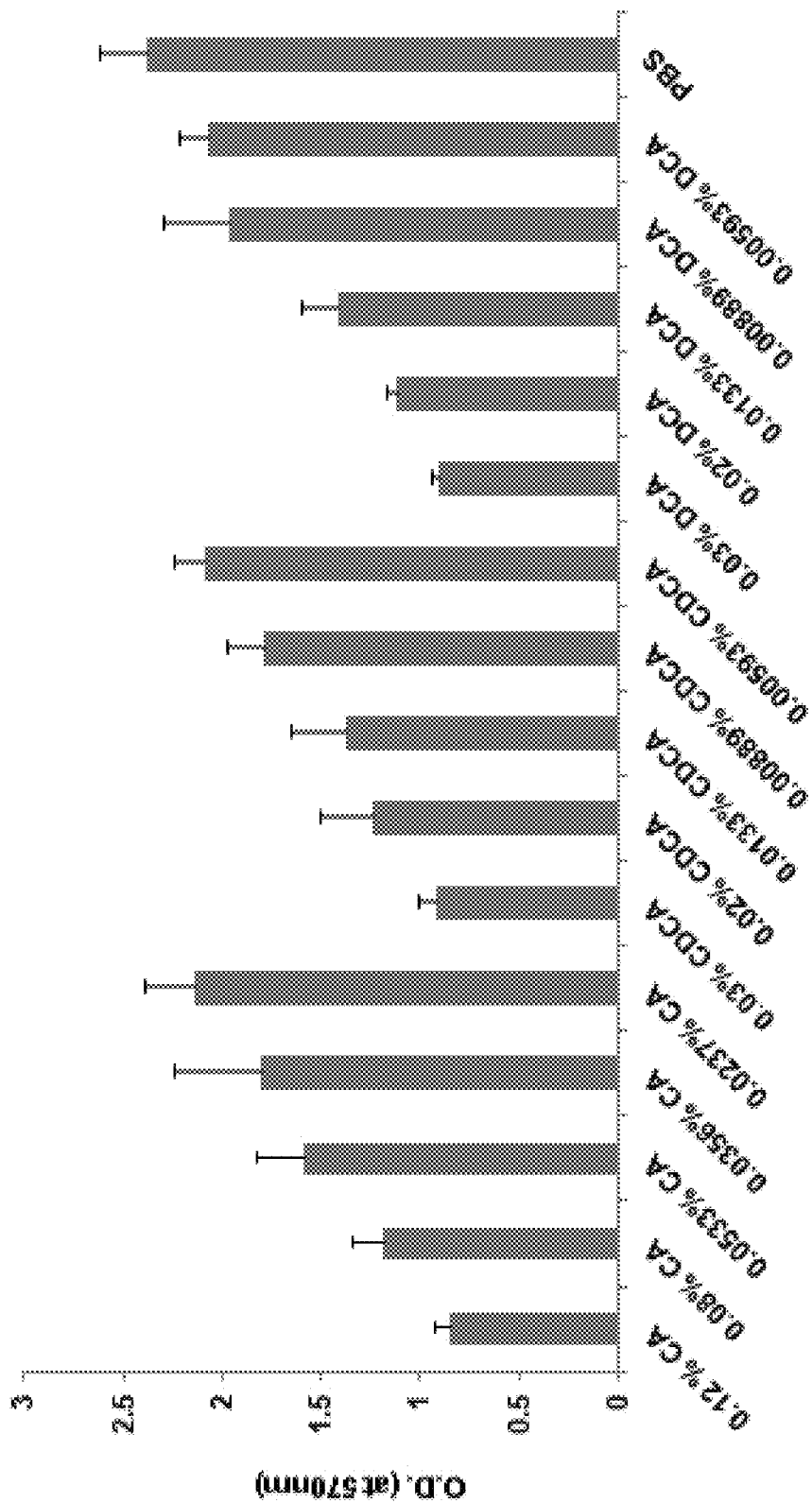
FIGS. 3A and 3B are charts showing measurement of fat pad lysis after treatment of DCA, CDCA, HDCA, and CA. 95~100 mg fat tissues were excised from diet induced obese mice and exposed to various concentrations of DCA, CDCA, and CA (FIG. 3A), and HDCA (FIG. 3B). Viability of fat tissues was measured by MTT assay and relative absorbance ($OD_{570}$) was measured by spectrophotometer. Increasing concentration of detergents produced more pronounced fat tissue lysis. The experiment was performed on five replicates for each treatment.
Figure 3B:
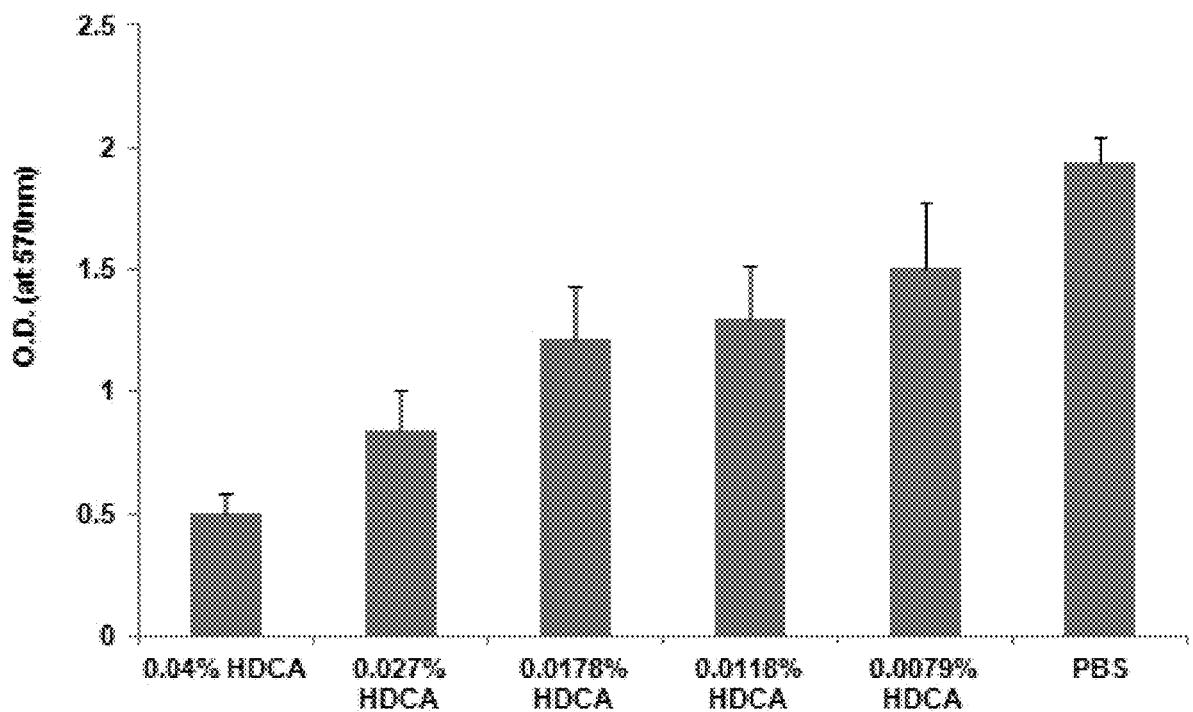

However, the results presented herein demonstrate that in vitro results do not always represent real in vivo situations. For example, a monolayer of cultured cells cannot reflect intact tissue structures. Because penetration into the intact tissues might affect cell lysis activity of bile salts, experiments were performed to test ex vivo adipose tissue lytic effect of DCA, CDCA, HDCA and CA in various concentrations. Subcutaneous fat tissues were freshly isolated from C57BL/6N mice that were fed high fat diet during 12 weeks. Fat tissues were incubated in the various concentrations of bile salt solutions for 10 minutes. Tissue lysis activities were measured by MTT assay (FIGS. 3A and 3B). All four bile salt solutions showed adipose tissue lysing effects. DCA and CDCA showed similar tissue lysing activity to that of the result from cultured cells. To compare the relative lysis activity of each bile salt in ex vivo condition, the $EC_{50}$ of DCA, CDCA, HDCA and CA was calculated. $EC_{50}$ concentrations of DCA, CDCA, HDCA and CA were 0.0179%, 0.0180%, 0.0250 and 0.0727%, respectively (Table. 2). Lysis activity of CA, HDCA was still lower than DCA or CDCA. However, $EC_{50}$ of CA was only 4 fold higher than DCA or CDCA, in contrast to the in vitro cell culture experiments, where the $EC_{50}$ of CA was about 7~8 fold higher than DCA and CDCA. Moreover, $EC_{50}$ of HDCA was only 1.4 fold higher than DCA or CDCA, in contrast to the in vitro cell culture experiments, where the $EC_{50}$ of HDCA was about 4~5 fold higher than DCA and CDCA.

TABLE 2

The EC50 values of bile salts required to lysis of fat tissues ex vivo.

| Detergent | ED50 (% w/v) |
|---|---|
| Deoxycholate (DCA) | 0.0179 |
| Chenodeoxycholate (CDCA) | 0.018 |
| Cholate (CA) | 0.0727 |
| Hyodeoxycholate (HDCA) | 0.0250 |

The result of the ex vivo study suggests that the lysis activities of bile salts cannot simply be estimated from in vitro results. Ex vivo conditions are more complex than in vitro conditions. For example, the structure of the tissues can affect the penetration of each bile salt to adipose cells and existence of internal structures in the tissues also can affect the lysis activity of bile salts. Compared to in vitro result, ex vivo results suggest that relatively lower concentration of CA or HDCA might be enough to lyse the adipose tissues. However, a 4 fold higher dose of CA may be required to get similar lipolysis activity with DCA or CDCA.

Figure 4:
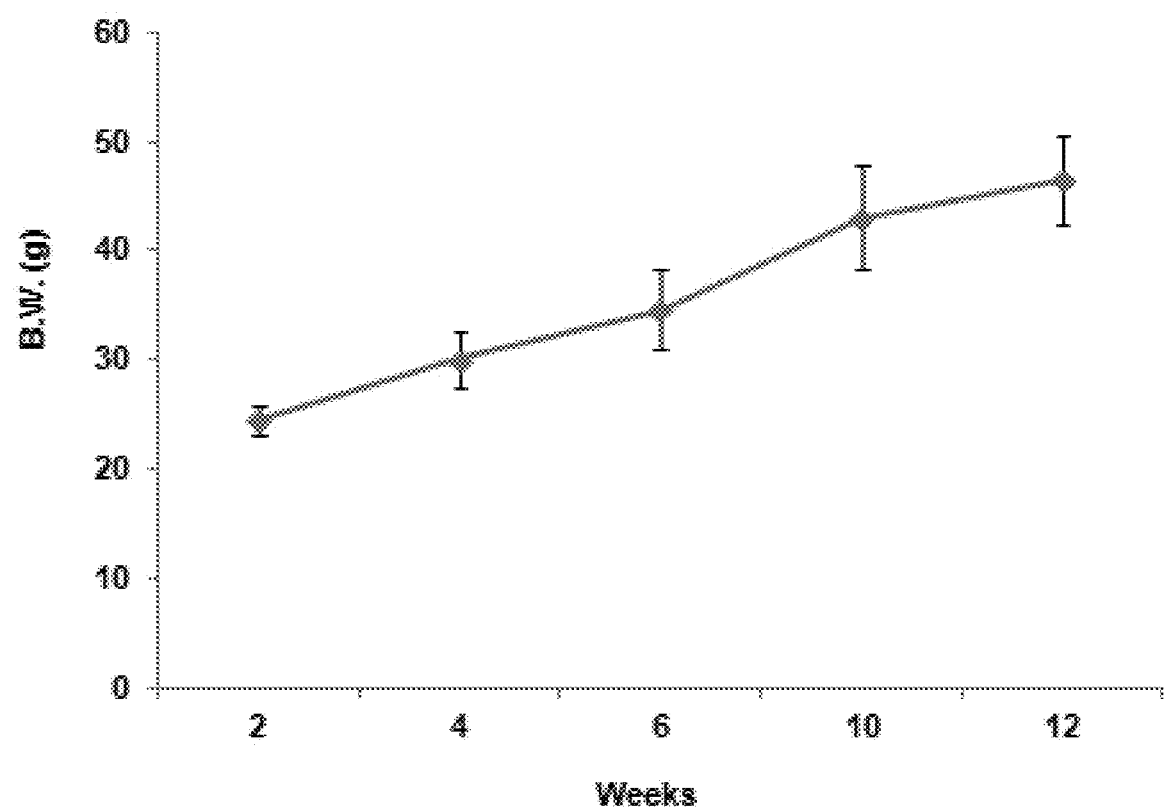
FIG. 4 is a graphs showing average body weight gain from the high fat diet fed mice. Body weight was monitored every two weeks.
Figure 5A:
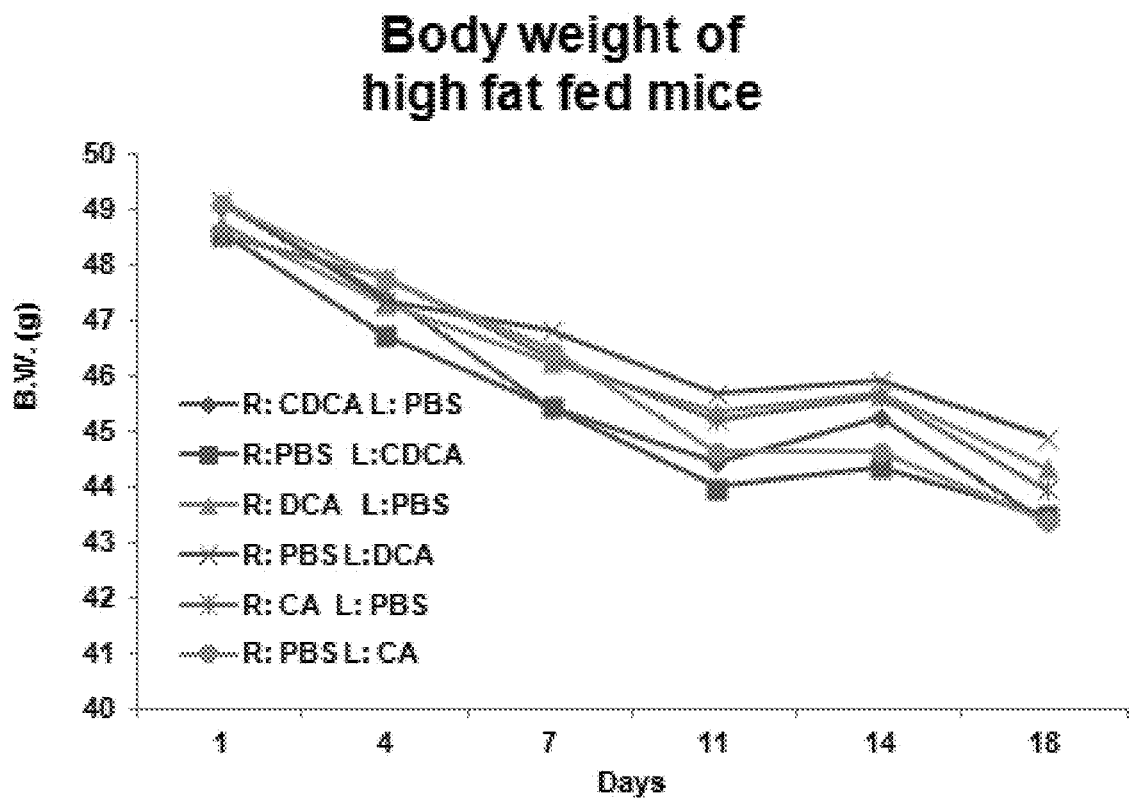
FIGS. 5A and 5B are charts showing (FIG. 5A) body weight and (FIG. 5B) inguinal fat pads weights of obese mice injected with 1% DCA, CDCA, CA, and phosphate buffered saline (PBS). Bile salts (DCA, CDCA and CA) solutions were injected to the right inguinal fat pads of mice. The left inguinal fat pads of mice were received with same volume of PBS as a control. Injections were repeated 4 more times during 2 weeks. Mice were sacrificed at 4 days after the final injection and inguinal fat pads were dissected and their weights were measured.
Figure 5B:
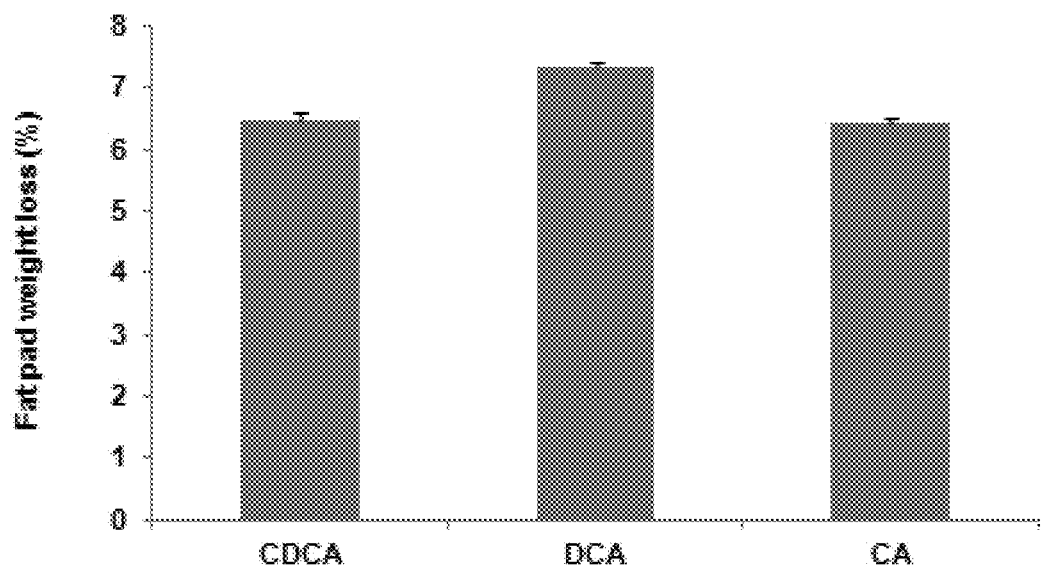

Based on the ex vivo results, it was hypothesized that if CA has a similar lytic activity against fat tissues compared with DCA or CDCA in in vivo or ex vivo conditions than in vitro, adverse events that occurred by damage of surrounding tissues can be differentiated from DCA or CDCA treatment. To test this, experiments were performed to examine the in vivo fat tissue-lytic activity of DCA, CDCA, and CA. Unlike in vitro and ex vivo conditions, in vivo conditions have even more complex aspects and many variables such as distribution, excretion and metabolism of administered drugs. Bile salt solutions were directly applied to subcutaneous fat tissues of obese mice. Obesity of mice was induced by feeding a 60% high fat containing diet to C57BL/6N mice. After the 12 weeks feeding of high fat, their body weights were reached to around 50 grams (FIG. 4). In one experiment, 1% of bile salt solutions were applied to inguinal fat tissues 5 times during 2 weeks. Compare with saline injected mice, bile salts injected mice showed reduced body weight and subcutaneous fat contents. Interestingly, reduced body weights and fat contents were similar with all three kinds of bile salts (FIGS. 5A, 5B).

Figure 6:
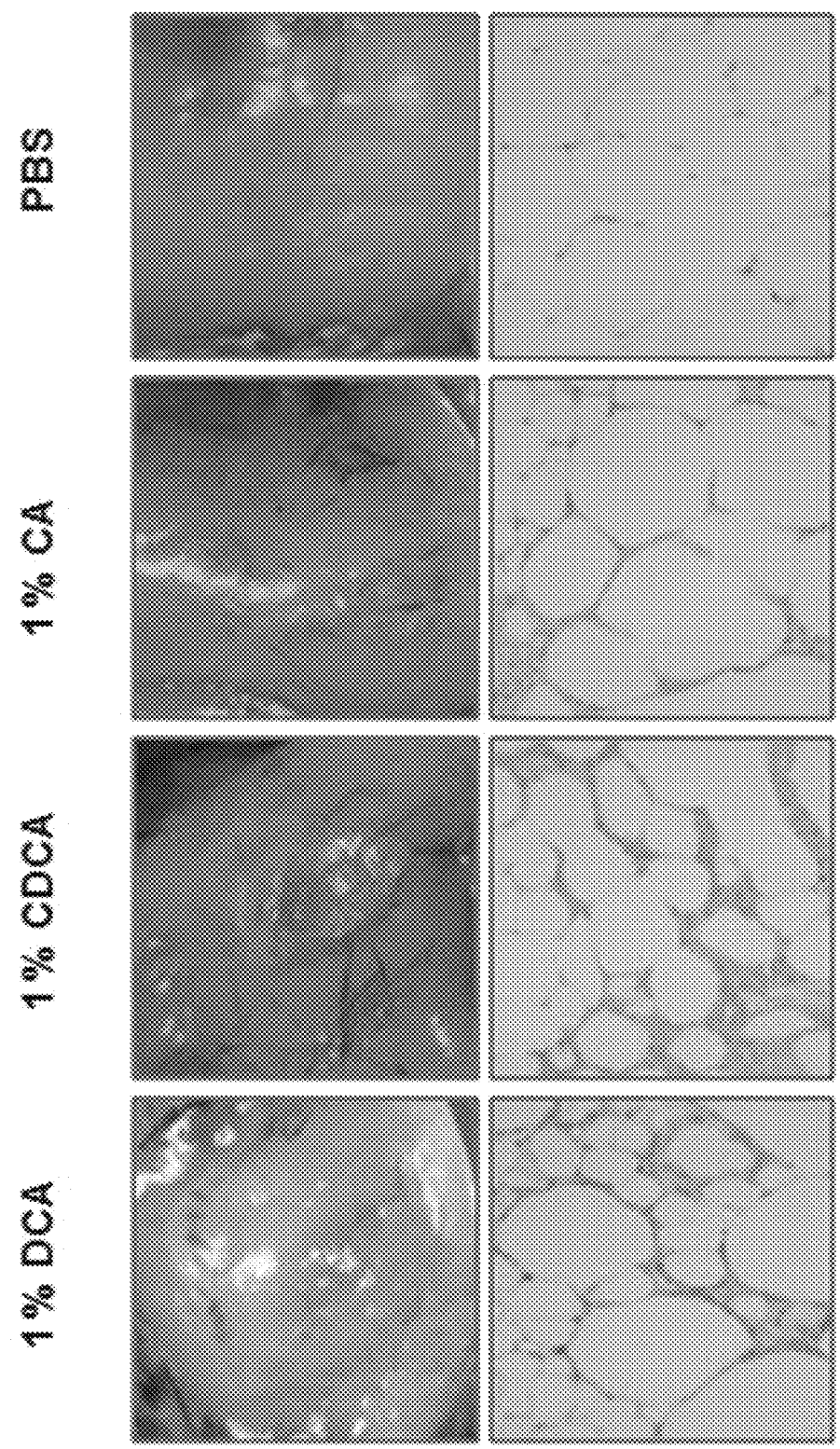
FIG. 6 is an image depicting the histologic changes observed in fat pads from bile salts administered mice. After bile salts and PBS injections, fat tissues of injected area were dissected. Dissected tissues were fixed with paraformaldehyde, embedded in paraffin blocks, and sectioned to slide glasses. Tissue damages and necrosis were observed by H & E staining.

To assure the tissue lytic activity of the bile salts, the injection sites of the subcutaneous fat tissues was observed (FIG. 6). There were no obvious abnormal lesions observed in the fat tissues from saline injected mice. Fat tissues from mice that received one of the bile salts (e.g., DCA, CDCA, and CA) showed yellowish lesions in the administered area, which represents necrotic inflammatory sites. The effects of bile salts on tissue histology were monitored by H & E staining of injected area. Injection of all three bile salts induced significant disruption of fat tissue organization compared to the case of saline. Fibrotic areas were observed in the injected area of DCA, CDCA, and CA. Without wishing to be bound by any particular theory, it is believed that repeated administration of bile salt may cause tissue fibrosis by recurrent inflammation.

These results indicate that all three bile salts have lipolytic activities in live mice and the in vivo effects of DCA, CDCA, and CA are similar at the same concentrations. In contrast to in vitro or ex vivo conditions, lipolytic effect from repeated administration with CA is compatible to the effects of DCA or CDCA in in vivo conditions.

Figure 7:
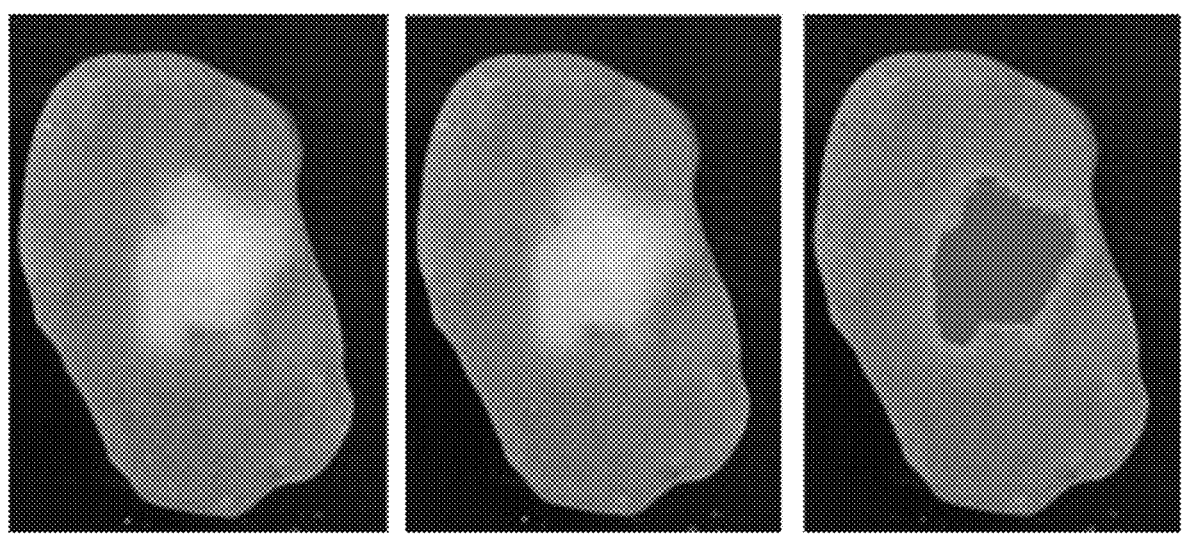
FIG. 7 is representative procedure of necrotic area measurement. Images of 2,3,5-tripheyltetrazolium chloride (TTC)-stained fat pad that obtained at 24 hours after injection. The normal tissue was stained red and the necrotic area was stained white and quantified using an image analysis system. The necrotic areas (white, unstained region) were measured using an image analysis system (ImageJ; National Institutes of Health, Bethesda, Md., USA).
Figure 8:
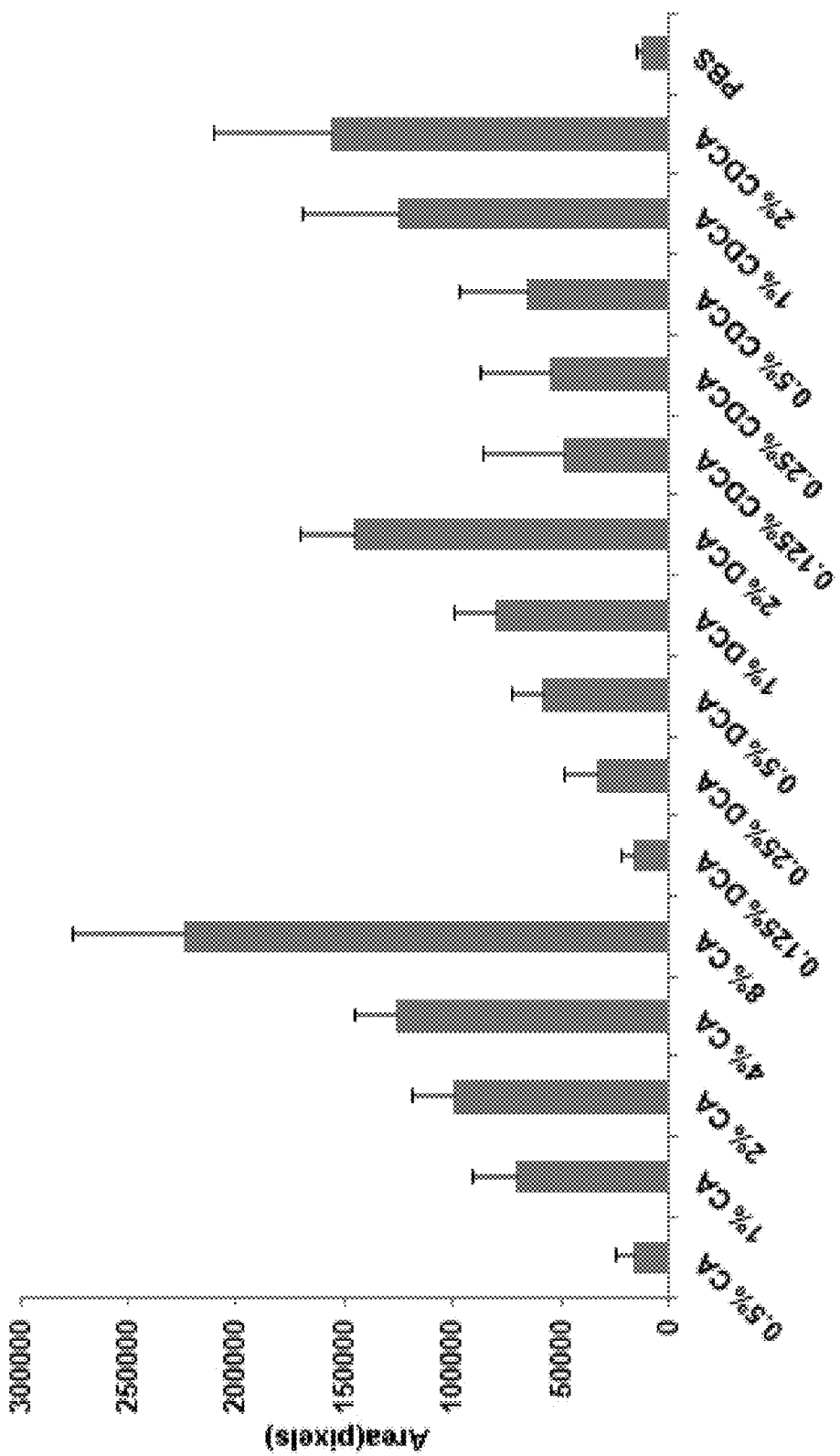
FIG. 8 is a chart showing quantitation of in vivo necrotic area. The fat pads injected by various concentration of bile salts (DCA, CDCA, and CA) and PBS were dissected and necrotic areas were determined by TTC staining (n=8 in each group). Increasing concentration of detergents produced more pronounced fat tissue lysis.
Figure 9:
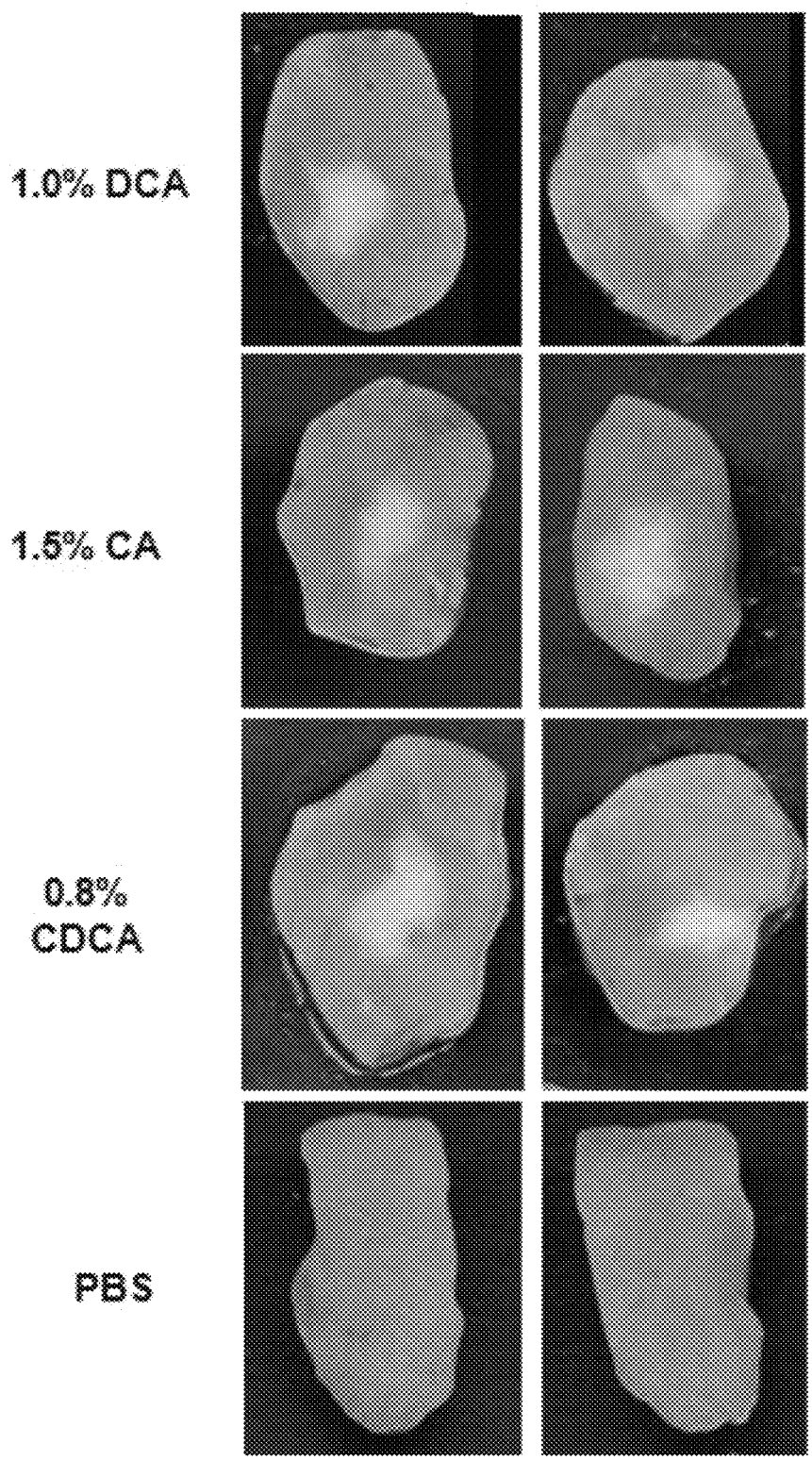
FIG. 9 is representative images of TTC-stained fat pad after treatment of various (DCA, CA, CDCA) bile salts and vehicle (PBS).

Although the reduction of body weight and fat mass in mice is attributable to bile salt treatment, it is believed that adverse effects from the injected bile salts and anesthetic procedures can also affect the weight loss in bile salt treated mice. To verify the in vivo effects of bile salts, tissue lytic activity of bile salts in live mice were directly monitored (FIG. 7 through FIG. 9).

To quantify the necrotic area of adipose tissue, a novel experimental method using TTC solution was developed. TTC is a redox indicator commonly used in biological experiments that especially indicate the area of infarction after ischemic shock. TTC is enzymatically reduced to red 1,3,5-triphenylformazan in living tissues due to the activity of various dehydrogenases, while it remains as white in areas of necrosis. After TTC staining, distinct boundaries were formed between necrotic white area and live red area (FIG. 7). White necrotic area easily measured by image analysis program. This novel method provides more precise calculation of tissue necrosis effect of chemicals, like bile salts, and enable the comparison of tissue lysis effects of various materials.

Various doses of DCA, CDCA or CA were injected to inguinal fat of obese C57BL/6N mice. After one day of a bile salt injection, necrotic areas of subcutaneous fats in injected mice were measured (FIG. 8 and FIG. 9). Increased concentration of injected bile salts caused proportional increment of necrotic areas. DCA and CDCA showed similar tissue necrosis in same dosages that reflect the in vitro and ex vivo data. Necrotic areas of CA treated mice were smaller than DCA or CDCA at the same concentration. However, about two fold higher concentration of CA is enough to show similar necrotic effects with DCA and CDCA. Representative images after DCA, CA, CDCA injection are presented in FIG. 9.

Collectively, tissue lysis effect of CA relative to DCA or CDCA was different in in vitro, ex vivo, and in vivo conditions. Generally, in vivo dosage effects from active reagents can be speculated by in vitro or ex vivo experiments. However, in many cases, unexpected effects in the bodies influence the real biological activities of reagents. Therefore, the in vitro or ex vivo results cannot easily be interpreted to in vivo conditions. The in vitro and ex vivo data presented herein show more than 4 fold high dose of CA is required to lyse the tissues compared with DCA or CDCA. However, the in vivo data demonstrate that such a higher dose of CA is not required for real fat lysis effects.

Figure 12A:
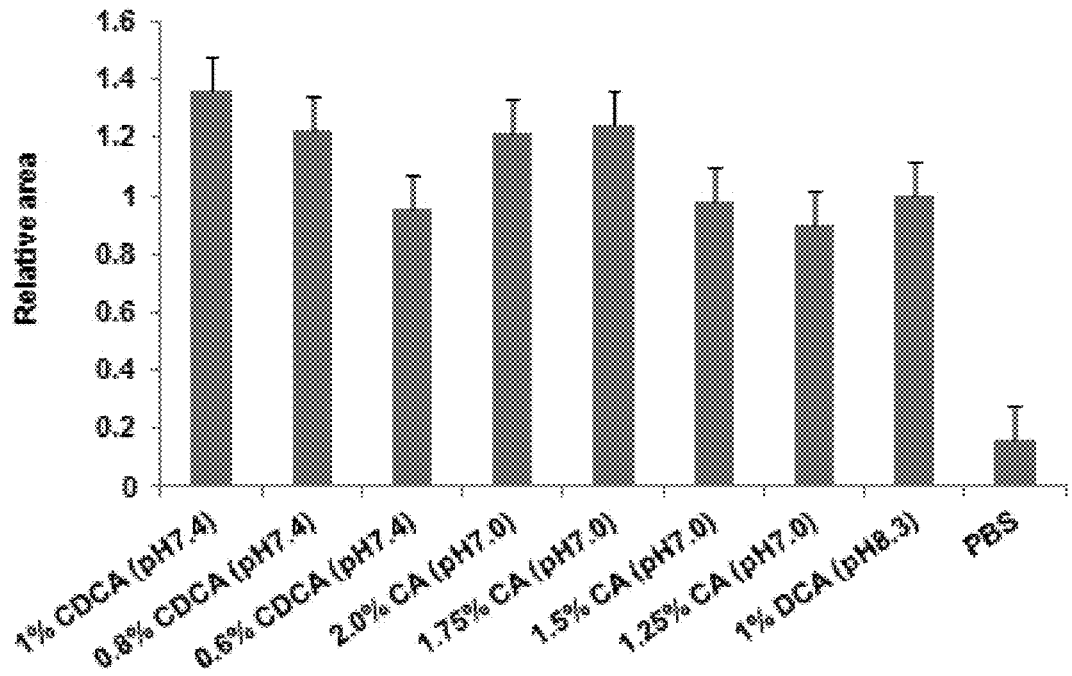
FIGS. 12A, 12B, and 12C are graphs showing relative necrotic area. The fat pads injected by various concentration of DCA, CDCA, and CA (FIG. 12A), UDCA (FIG. 12B), HDCA (FIG. 12C) were dissected and necrotic areas were determined by TTC staining (n=10 in each group). The necrotic areas (white, unstained region) were measured using an image analysis system. Injection of higher concentration of detergents produced more pronounced fat tissue lysis.
Figure 12B:
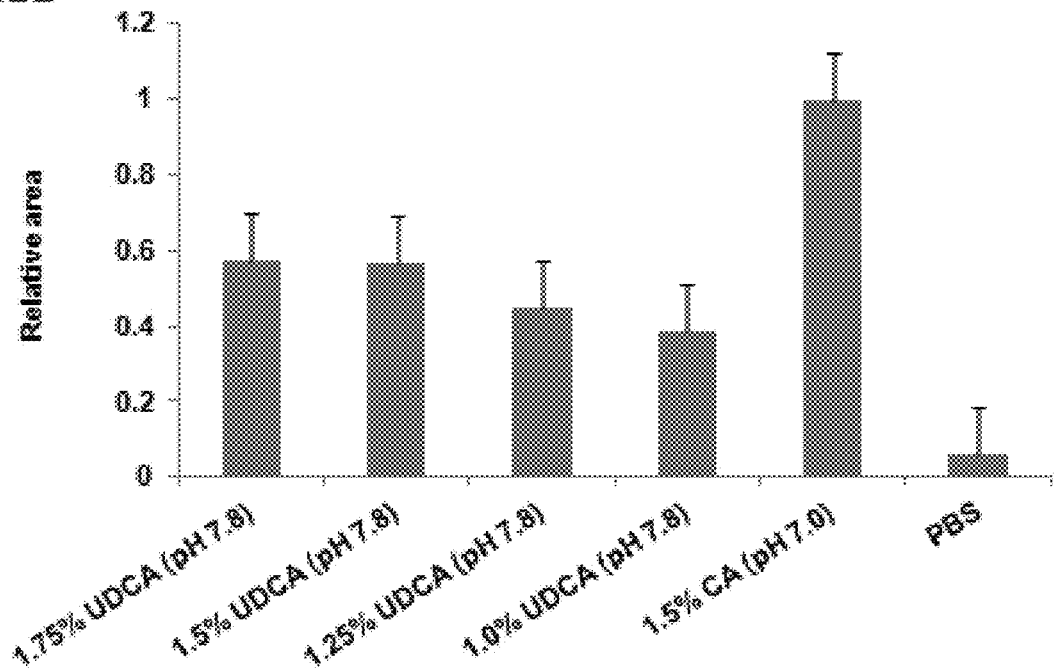
Figure 12C:
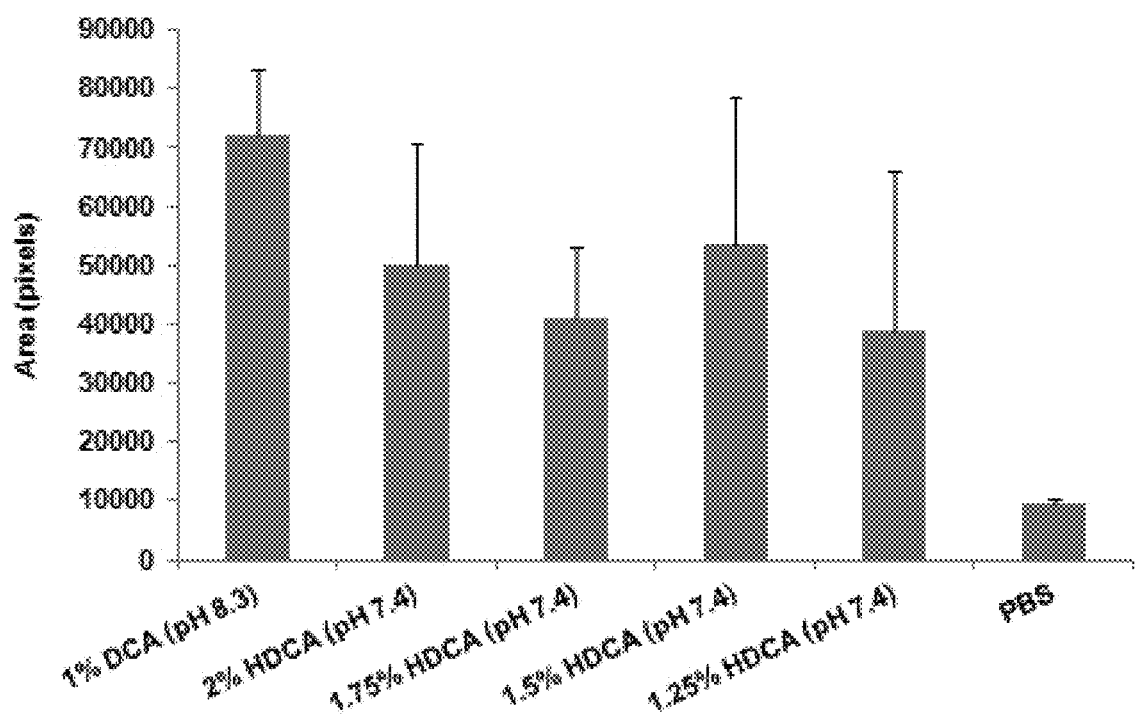

6.7, 7.0, 7.2, 7.4, 7.6, 7.8, 8.0, 8.3 at 25° C.) conditions (FIGS. 12A, 12B, and 12C). In lower pH, precipitation or gelation of bile salts were observed. Aqueous solution of DCA, CDCA, HDCA, UDCA and CA remained stable in pH lower than 8.3, 7.4, 7.4, 7.8 and 7.0, respectively (Table 3). Generally, the discomfort or pain at the injection site is caused by the solution of lower or higher pH than normal physiologic pH. Because CDCA, HDCA and CA have a stable properties at normal pH, their use as ingredients of injections is expected to reduce the discomfort and pain than other bile salts, such as DCA and UDCA.

TABLE 3

Solution stability of bile salt in various pH (25° C., 1% in 10 mM phosphate buffer)

| | pH | | | | | | | | |
|---|---|---|---|---|---|---|---|---|---|
| | 6.5 | 6.7 | 7.0 | 7.2 | 7.4 | 7.6 | 7.8 | 8.0 | 8.3 |
| DCA | Gelation | Gelation | Gelation | Gelation | Gelation | Gelation | Gelation | Gelation | Stable |
| CA | Precipitation | Precipitation | Stable | Stable | Stable | Stable | Stable | Stable | Stable |
| CDCA | Gelation | Gelation | Gelation | Precipitation | Stable | Stable | Stable | Stable | Stable |
| HDCA | Gelation | Gelation | Gelation | Gelation | Stable | Stable | Stable | Stable | Stable |
| UDCA | Precipitation | Precipitation | Precipitation | Precipitation | Precipitation | Precipitation | Stable | Stable | Stable |

Detergent activities of bile salts represent the solubilizing power of lipid or proteins. Therefore, it is expected that the cell lysis activity is proportional to the activity of detergent. Because, DCA and CDCA have stronger detergent activity than CA, they also show higher cell lytic activity. Nevertheless, in vivo cell lytic activities of bile salts are not simply representing the detergent power of bile salts. This unexpected fat lysing effect of CA enables the use of CA as an active component of lipolysis injection, particularly at a concentration that was not predicted from the in vitro and ex vivo results.

Figure 10A:
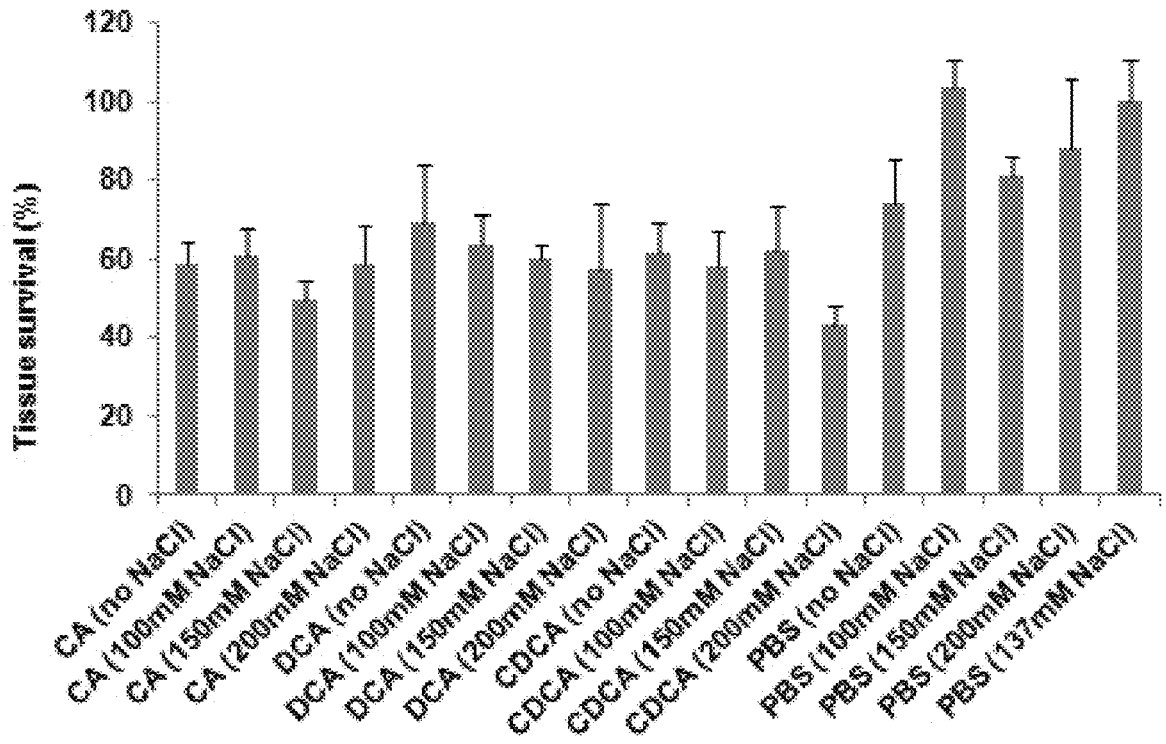
FIGS. 10A and 10B are graphs depicting tissue viability compared to normal PBS (FIG. 10A) and relative absorbance (FIG. 10B) after MTT assay. Mice inguinal fat pads were exposed in various concentrations of salt (0~200 mM sodium chloride) in phosphate buffer that containing CA, DCA and CDCA. 95~100 mg fat tissues were incubated with $EC_{50}$ concentration (Concentrations that show 50% reduction of tissue viability in normal PBS) of DCA, CDCA, and CA in various salt concentrations. The experiment was performed on five replicates for each treatment.
Figure 10B:
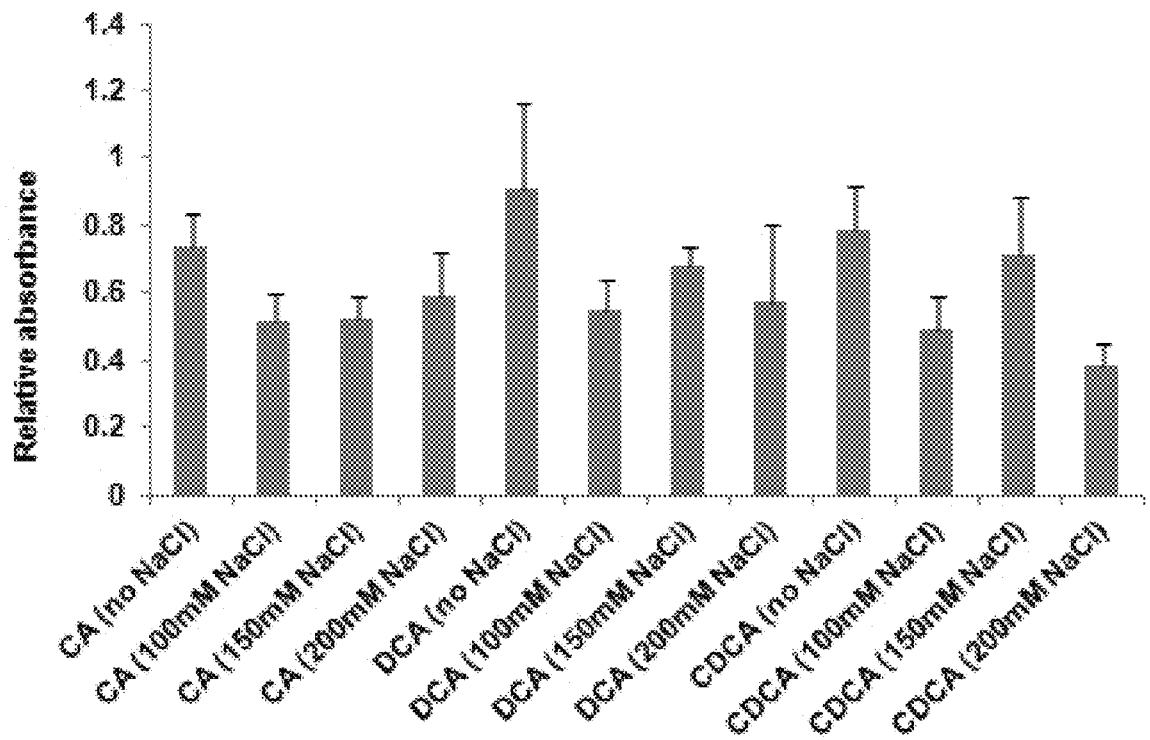
Figure 11A:
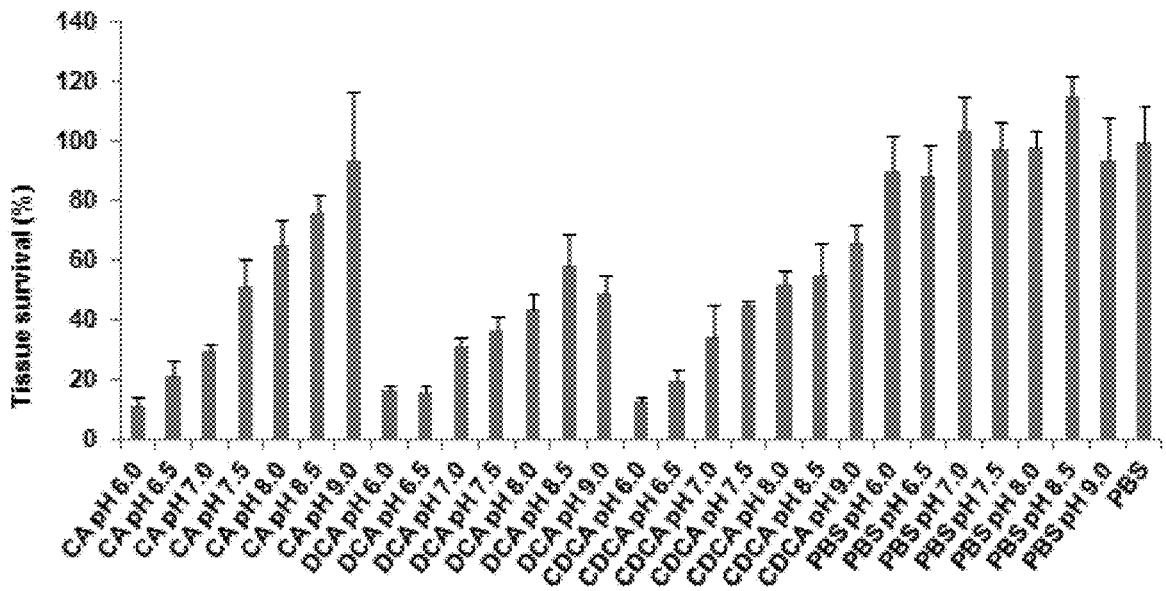
FIGS. 11A, 11B, 11C, and 11D are images showing viability (FIGS. 11A, 11C) and relative absorbance (FIGS. 11B, 11D) of mouse inguinal fat pad exposed in various pH conditions (pH 6.0, 6.5, 7.0, 7.5, 8.0, 8.5, 9.0) with DCA, CDCA, CA, HDCA, and PBS. 95~100 mg fat tissues were incubated with $EC_{50}$ concentration of DCA, CDCA, HDCA, and CA in various pH conditions. Viability of fat tissues was measured by MTT assay and absorbance ($OD_{570}$) was measured by spectrophotometer. The experiment was performed on five replicates for each treatment.
Figure 11B:
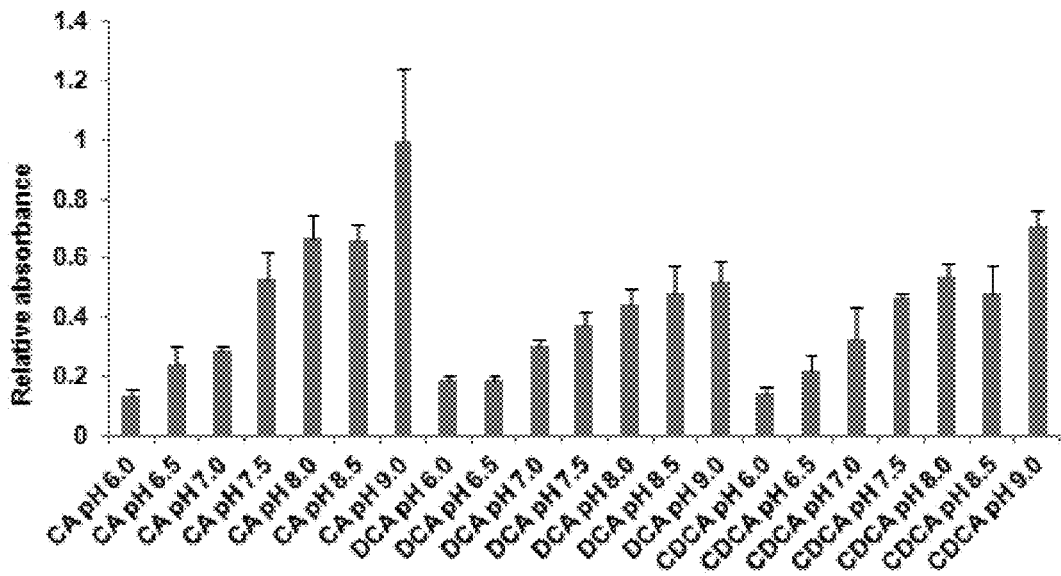
Figure 11C:
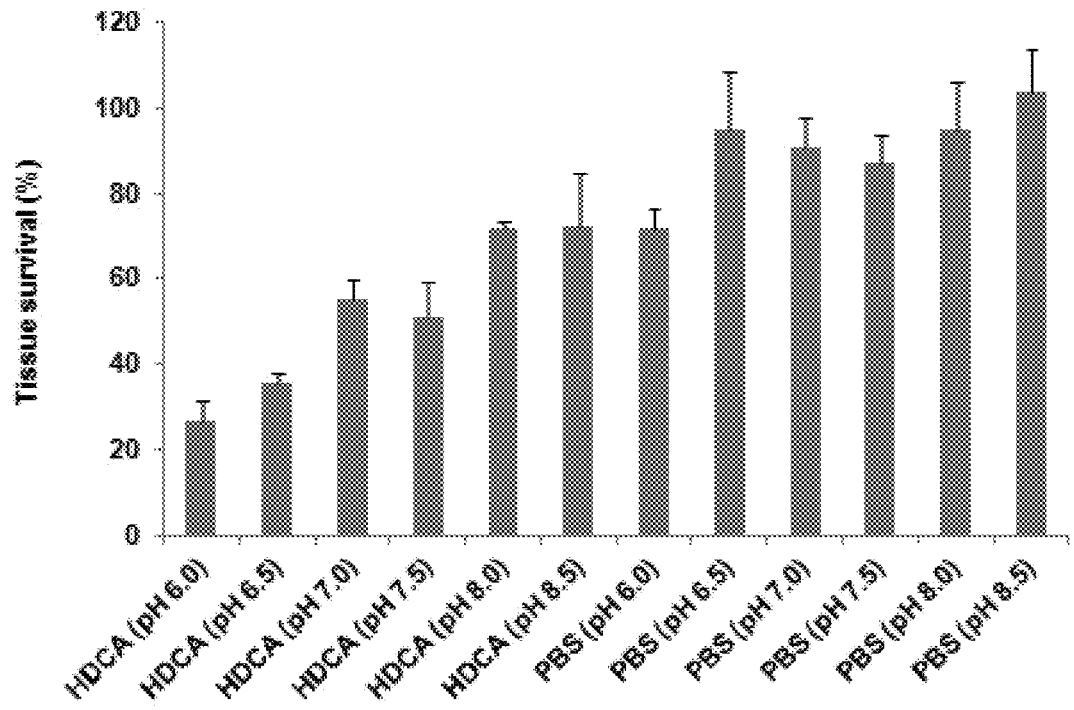
Figure 11D:
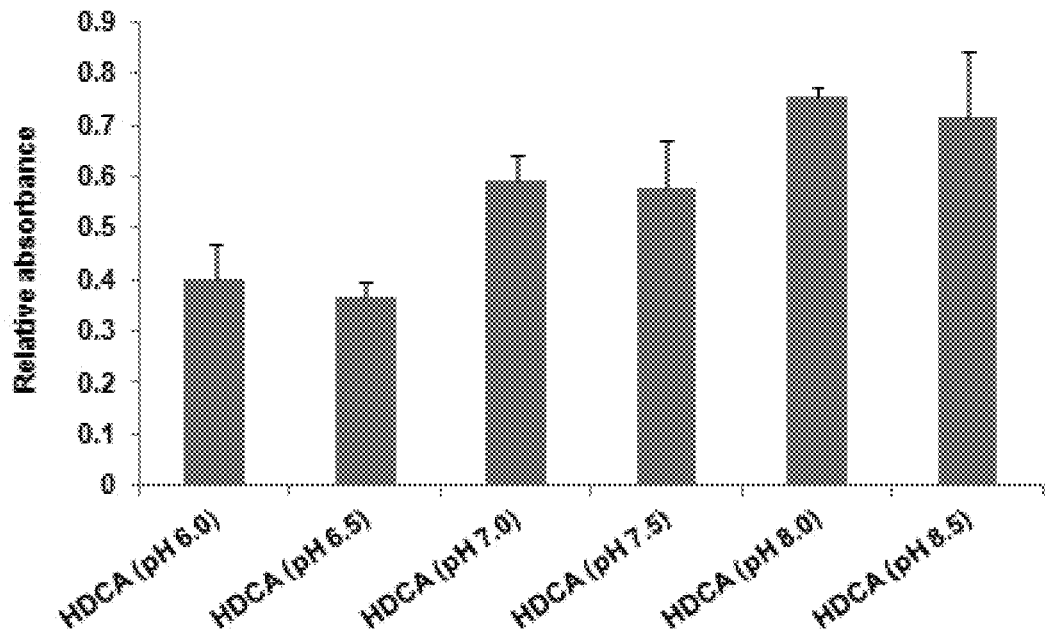

The concentration of salt in solution also can affect the detergent activity of bile salt. The effect of concentration of sodium chloride on the fat lysis activities of bile salts was tested. Inguinal fat tissues from diet induced obese mice were incubated in various solutions containing different concentration of sodium chloride. Concentration of each bile salt was adjusted to the $EC_{50}$ in pH 7.4. However, treatment of various concentration of sodium salt did not make any differences of the fat lysis activities of individual bile salts (FIGS. 10A and 10B).

The pH of detergent solutions can influence the formation of micelles and detergent activity. To test the effect of pH of bile salts on the fat lysis activities, inguinal fat tissues from diet induced obese mice were incubated in various pH conditions (pH 6.0~pH 9.0) of DCA, CDCA, HDCA and CA. pH of bile salt solutions were adjusted by phosphate buffer. Concentration of each bile salt was adjusted to the $EC_{50}$ in pH 7.4. Interestingly, increased pH of solution greatly diminishes the fat lysis activities of CDCA, HDCA and CA (FIGS. 11A, 11B, 11C, and 11D). In the case of DCA, precipitation of DCA was observed in lower pH solutions. As a result, higher pH buffers of DCA do not show greatly decreased fat lysis activity compared to the cases of CA, HDCA or CDCA. CA and CDCA solutions above the pH 9 mostly lost their fat lysis activities. Therefore, pH lower than 9 was required for the efficient fat lysis using CA or CDCA solutions.

The stability of bile salt was affected by pH of solution. Experiments were performed to test the stabilities of 1% (w/v) bile salts in various phosphate buffer (10 mM; pH 6.5, Considering that DCA solution is not stable in physiologic pH, the formulation of DCA solution for lipolysis injection must be higher than pH 8.3. Bile salt solution having higher pH shows lower tissue lysis activity. Because CA, CDCA, UDCA, and HDCA solution is stable at lower pH, it is expected that smaller amount of CA, CDCA, UDCA and HDCA is enough to show similar tissue lytic effect with high pH DCA solution. To test this, concentrations that show similar tissue lytic activity with 1% of DCA solution in condition of pH 8.3 were selected by monitoring of tissue necrotic area after the injection of CA (pH 7.0) and CDCA (pH 7.4) solution at various concentrations. It was observed that the tissue lysis activity of DCA solution in condition of pH 8.3 was lower than the activity of DCA preparation in condition of pH 7.4. In same pH (pH 7.4) condition, the injection of about 2% CA or 1% CDCA solution showed similar tissue lysis activity with the injection of 1% DCA. However, the concentration of 1.5% CA (pH 7.0) or 0.6% CDCA (pH 7.4) were enough to show similar tissue lysis effect with 1% DCA, having higher pH (pH 8.3) (FIG. 12A). Bile salt solution of physiological pH and low concentration can give additional advantages such as reduction of adverse events.

Figure 13A:
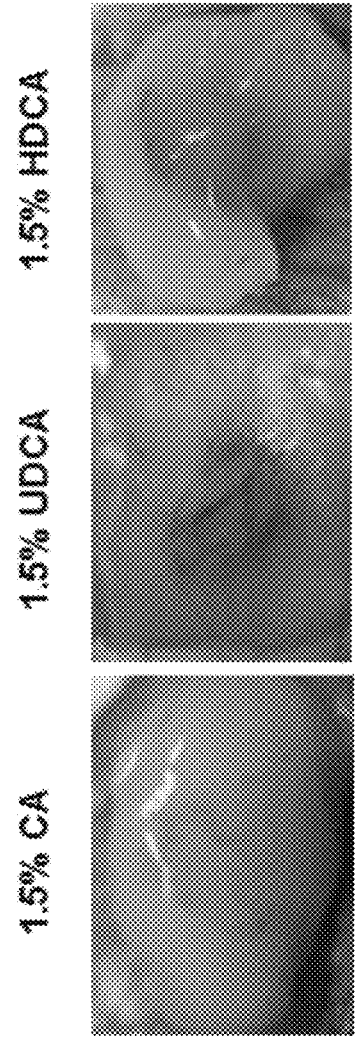
FIGS. 13A and 13B are images showing the histological changes observed in mice fat pads after administration of bile salts. Fat tissues were dissected and fixed with paraformaldehyde, embedded in paraffin blocks, and sectioned to slide glasses after the injection of 1.5% CA, 1.5% HDCA, and 1.5% UDCA solution. Infiltration of polymorphonuclear (PMN) cells into the fat pad tissue was observed in HDCA or UDCA treated tissues by H & E staining.
Figure 13B:
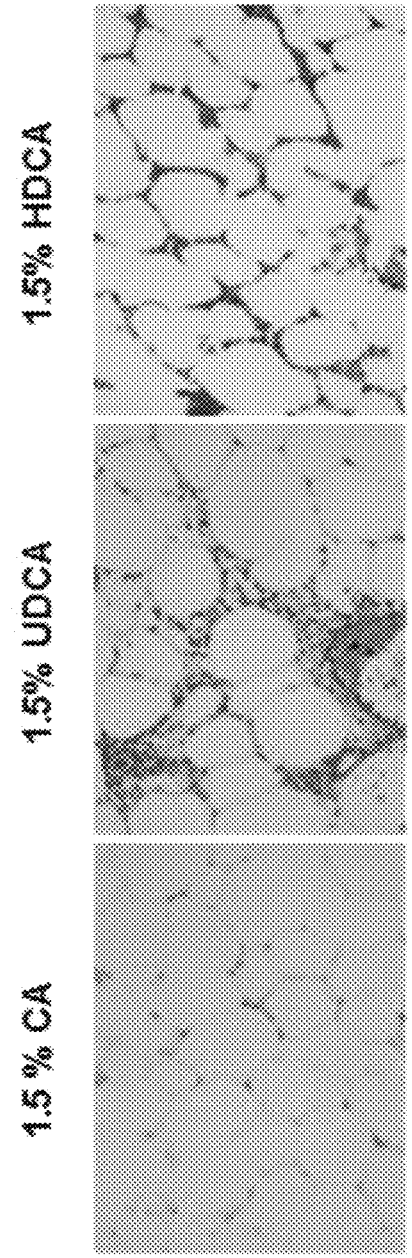
Figure 14A:
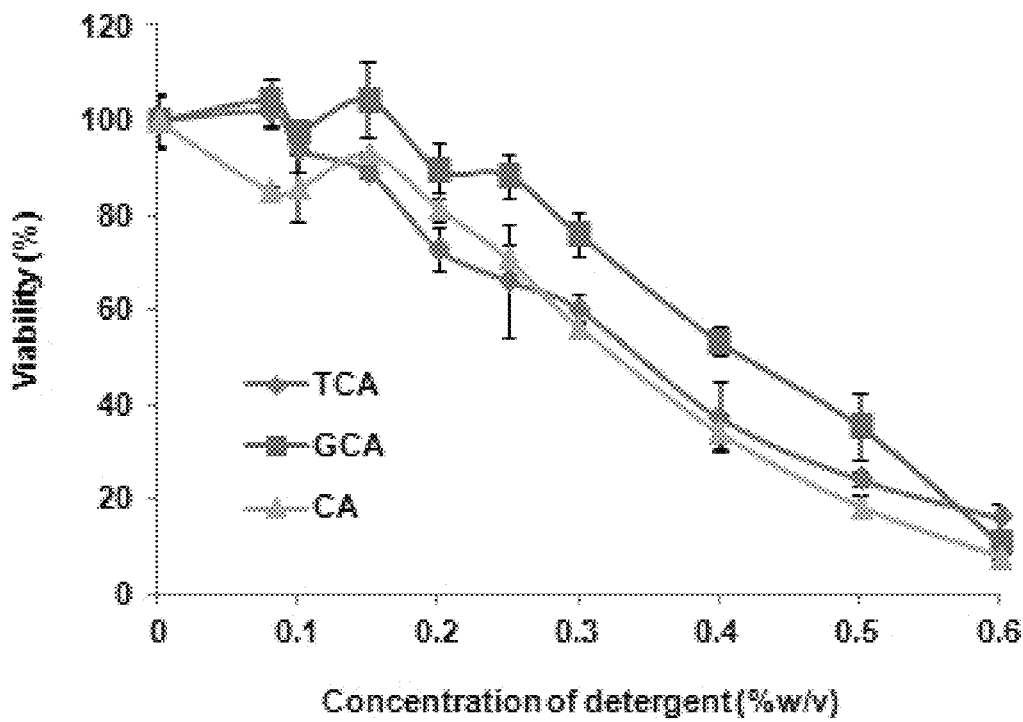
FIGS. 14A, 14B, and 14C are charts showing cell lysis effects of various bile salts in 3T3-L1 adipocytes. Differentiated 3T3-L1 adipocytes were exposed to taurocholate (TCA), glycocholate (GCA), CA, taurodeoxycholate (TDCA), glycodeoxycholate (GDCA), DCA, taurochenodeoxycholate (TCDCA), and CDCA (FIGS. 14A-14C) for 1 hour and cell viability was measured by MTT assay. All detergents show dose-dependent cell lysis effects. Conjugation of taurine, glycine does not affect the cell lytic activities of CA, DCA, and CDCA. The experiment was performed on three replicates for each treatment. Results are expressed as total percentage of viable cell as compared with untreated control.
Figure 14B:
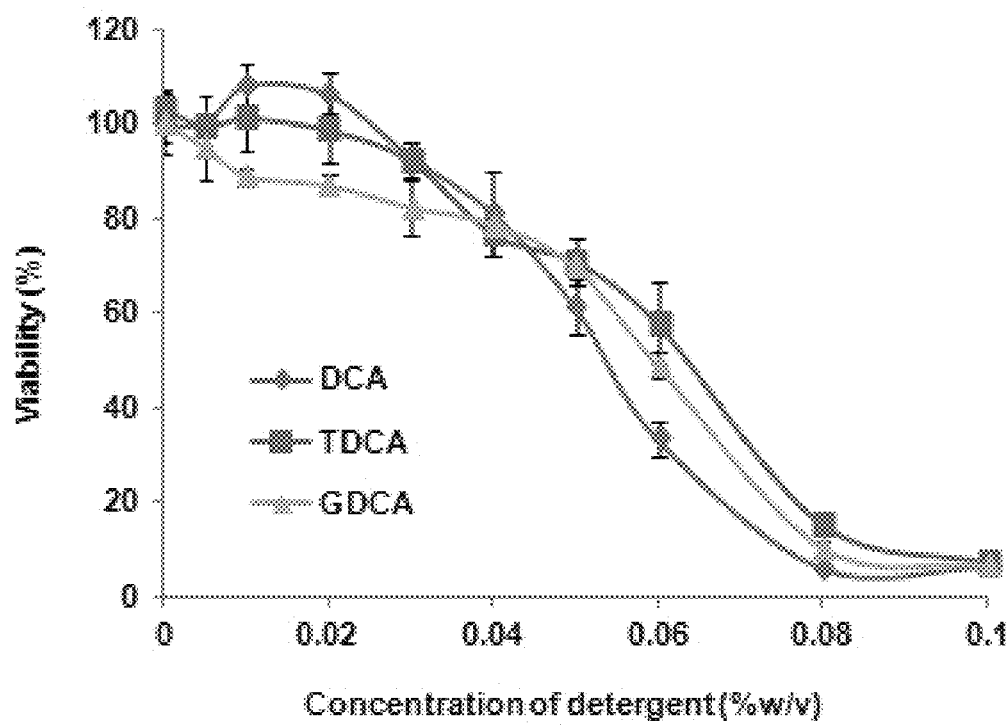
Figure 14C:
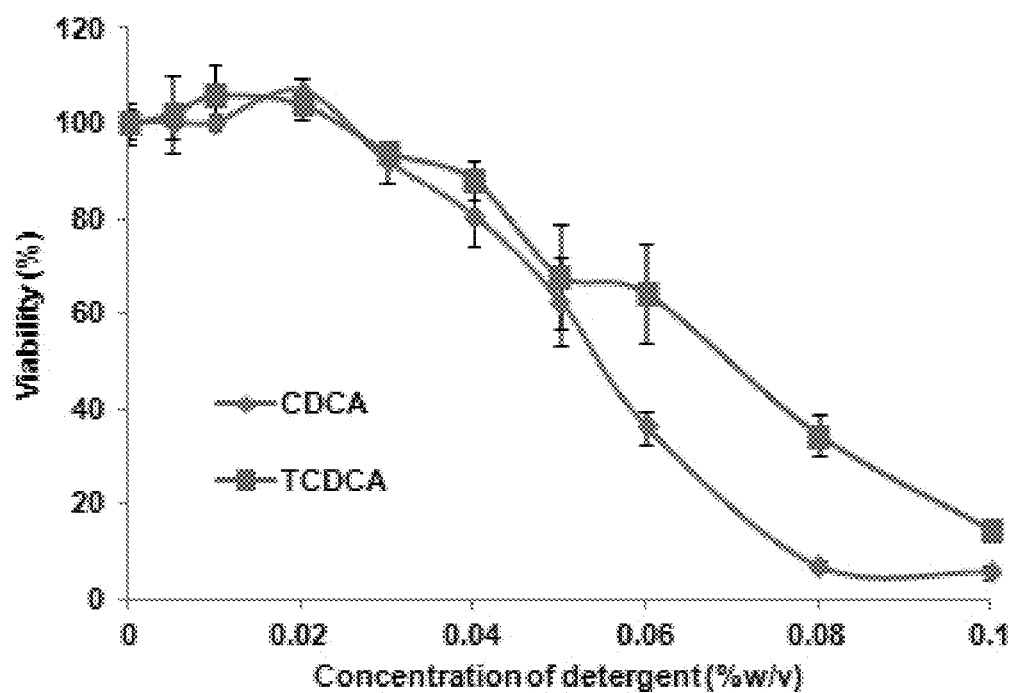
Figure 15A:
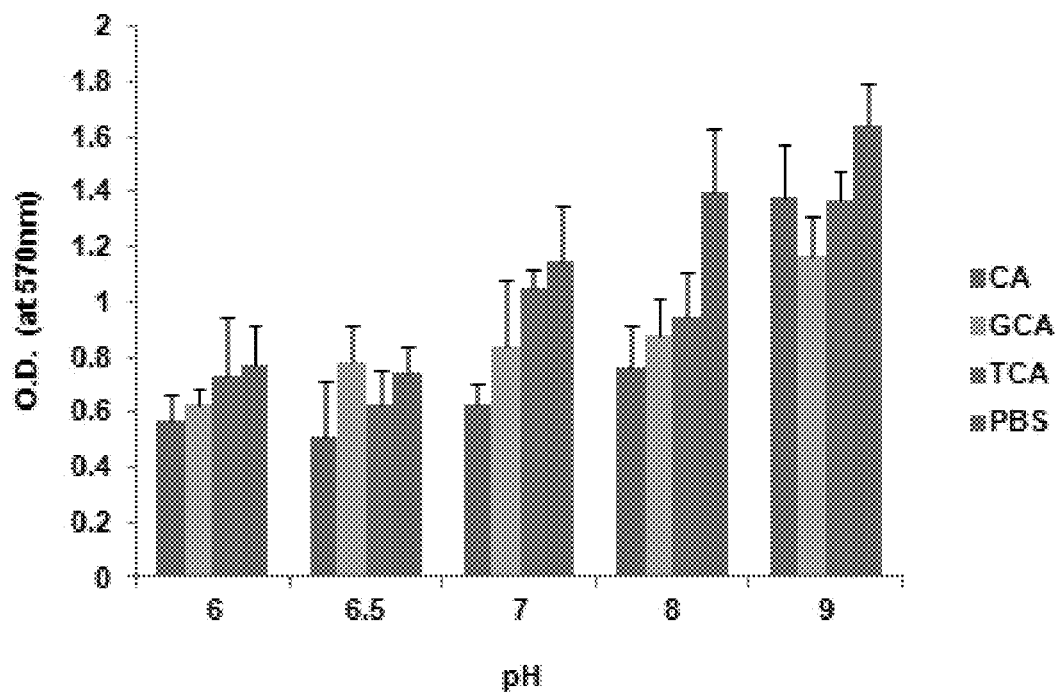
FIGS. 15A and 15B are images showing tissue viability of mouse inguinal fat pad exposed in various pH conditions (pH 6.0, 6.5, 7.0, 8.0, 9.0) of CA, GCA, TCA solutions and vehicle (PBS). 95~100 mg fat tissues were incubated with 0.1% GCA, TCA and CA in various pH conditions. Viability of fat tissues was monitored as optical density (FIG. 15A) and relative absorbance (FIG. 15B) by MTT assay. Optical density (FIG. 15A) and relative absorbance (FIG. 15B) The experiment was performed on five replicates for each treatment.
Figure 15B:
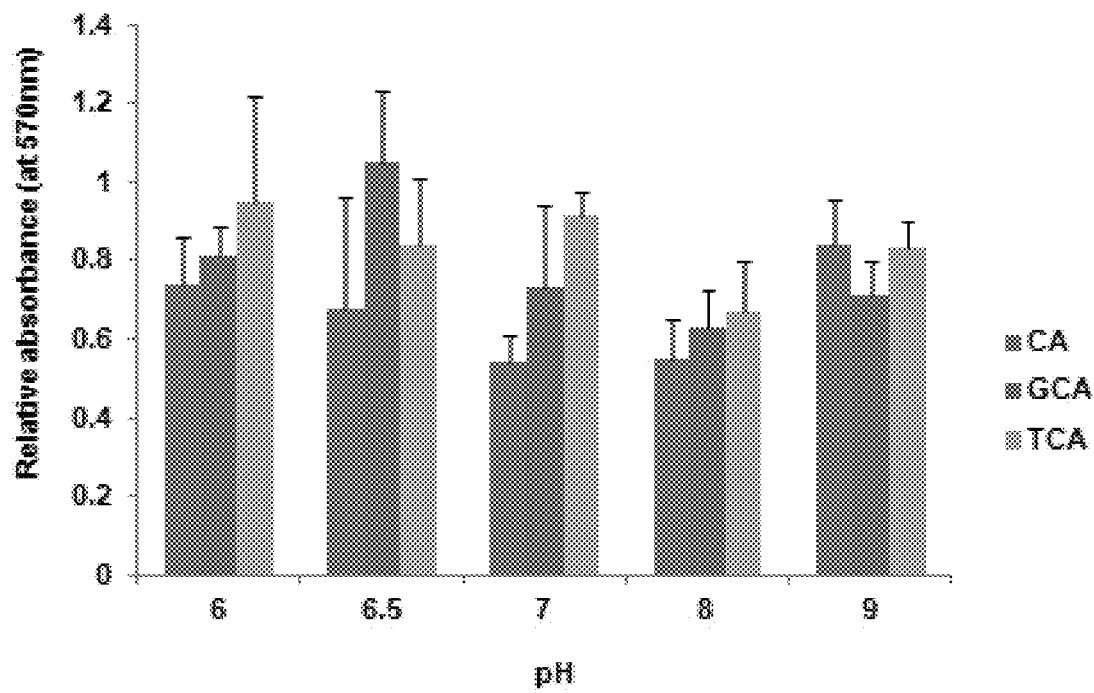

Unlikely with CDCA and CA, tissue lysis effect of UDCA or HDCA did not increased proportionally with higher concentration of UDCA or HDCA (FIGS. 12B and 12C). Interestingly, one time injection of UDCA or CDCA to the subcutaneous fat induces yellowish structure in injected site (FIG. 13A). H&E staining shows that infiltration of large amount of polymorphonuclear (PMN) cells in injection sites (FIG. 13B). Yellowish structures were expected to the results of formation of PMN-rich exudates (pus) after UDCA or HDCA injection. Infiltration of PMN cells and inflammation by UDCA or HDCA injection might be a factor affecting the necrotic activities of UDCA or HDCA. Observation of severe inflammation after injection of UDCA or HDCA to subcutaneous fat shows that UDCA or HDCA is not suitable to use as an ingredient of lipolysis injection.

Bile salts are conjugated with taurine or glycine in the liver. It was tested that the conjugation with taurine or glycine to bile salts has any effect to the adipose cell lysis activities. Glycine or taurine conjugated forms of CA, CDCA and DCA were treated to the differentiated adipose cells (FIGS. 14A, 14B, 14C, 15A, and 15B). Cell lysis activities of glycine or taurine conjugated bile salts were almost same with non-conjugated forms of bile salts. These results show that there is almost no effect to the cell lysis activity by the conjugation of glycine or taurine with bile salts.

Figure 16:
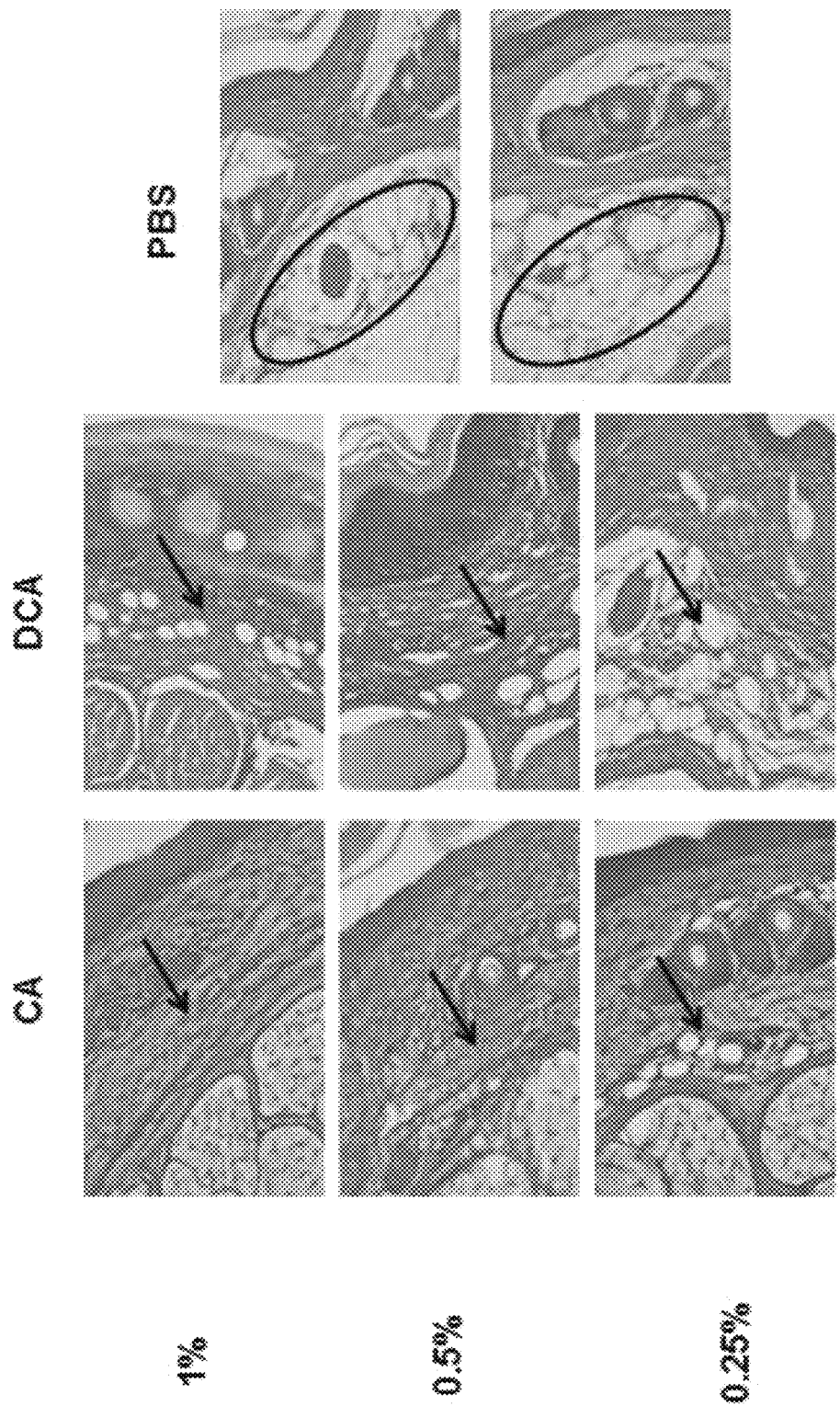
FIG. 16 is a series of images showing histologic examination of mice tails 14 days post-injection of DCA, CA, and PBS. H&E staining shows necrosis of the subcutaneous fat in the treated tail. The tissue architecture of the muscle and skin layer also observed in treated tails.

Different aspects of fat lysis in various conditions also can be occurring in other tissues. Although there is no big difference in the lysis effects of adipose cells with the effects of muscle cells in in vitro conditions, individual tissue lytic activities can vary in in vivo conditions. Therefore, if some bile salts can result in reduced skin or muscle lysis activities compared to adipose tissues, lipolytic reagents having increased safety can be developed. To test this, various concentrations of DCA and CA in a pH 7.4 solution were injected to the tails of mice and the tissue integrities of the tails was evaluated (FIG. 16). Because, tails are comprised of fat, muscle and skin, the integrity of individual tissue layers can be easily monitored at one time. Fat layers of tails are disrupted by both DCA and CA injection compared to saline injection. Interestingly, the damages of muscles are prominent in DCA injected tails compared to the same concentration of CA injected tails. Skin layers of DCA or CA injected mice were not severely damaged in both cases.

Figure 17A:
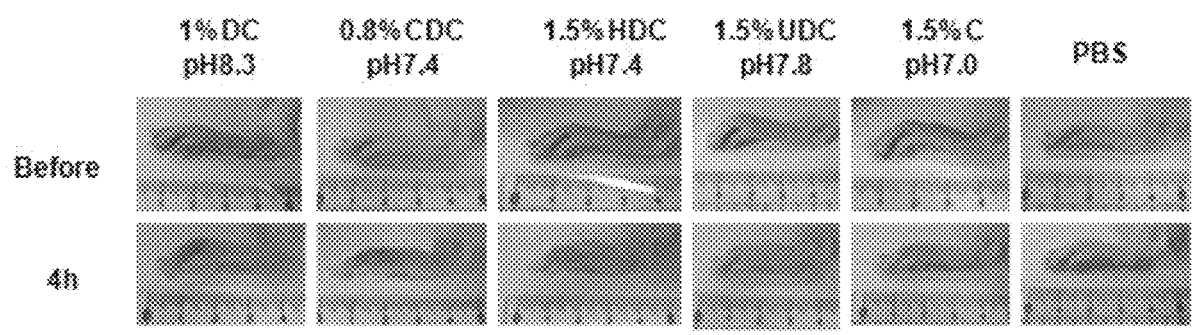
FIGS. 17A, 17B, 17C, and 17D are images showing appearance of rat paws (FIGS. 17A, 17C) and paw thickness (FIGS. 17B, 17D, 17E) after the injections of 1% DCA, 1.5% CA, 0.8% CDCA, 1.5% UDCA, 1.5% HDCA and PBS into the hind paws.
Figure 17B:
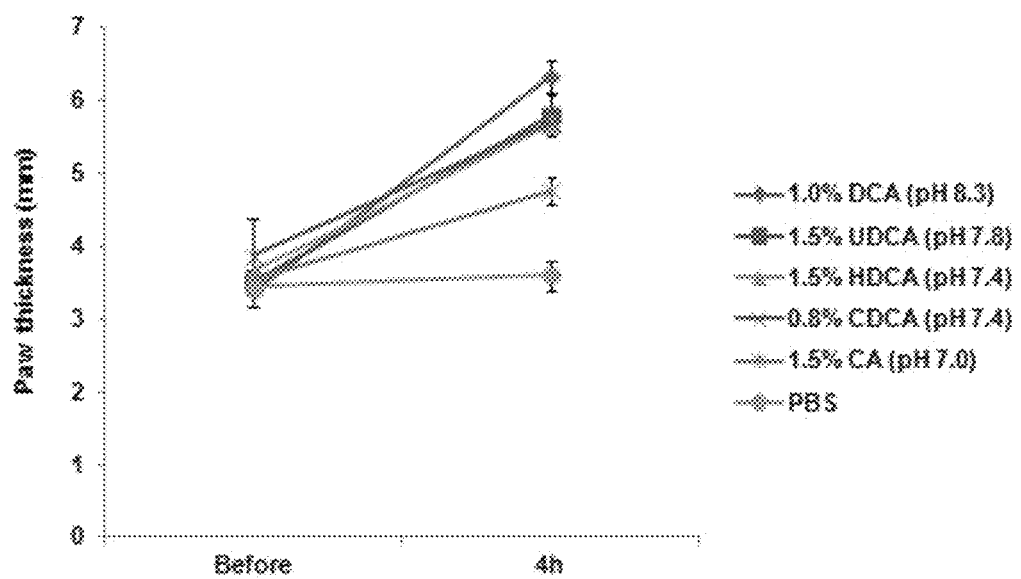
Figure 17C:
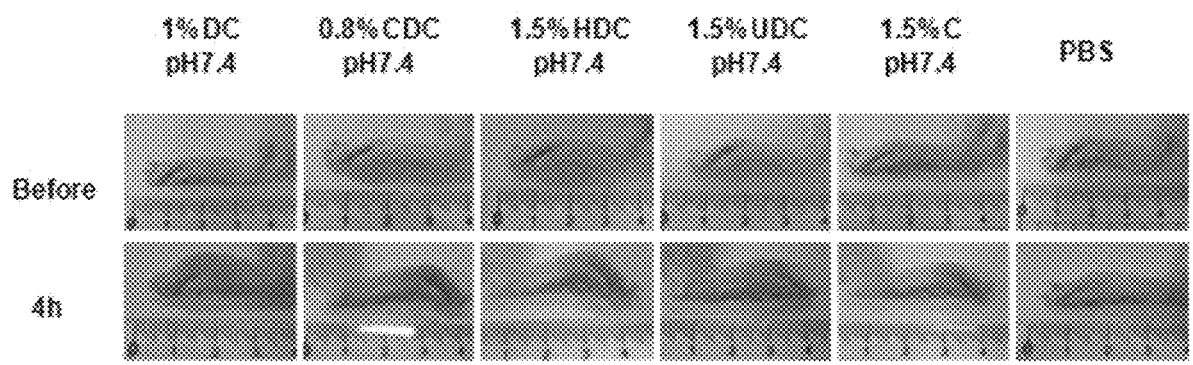
Figure 17D:
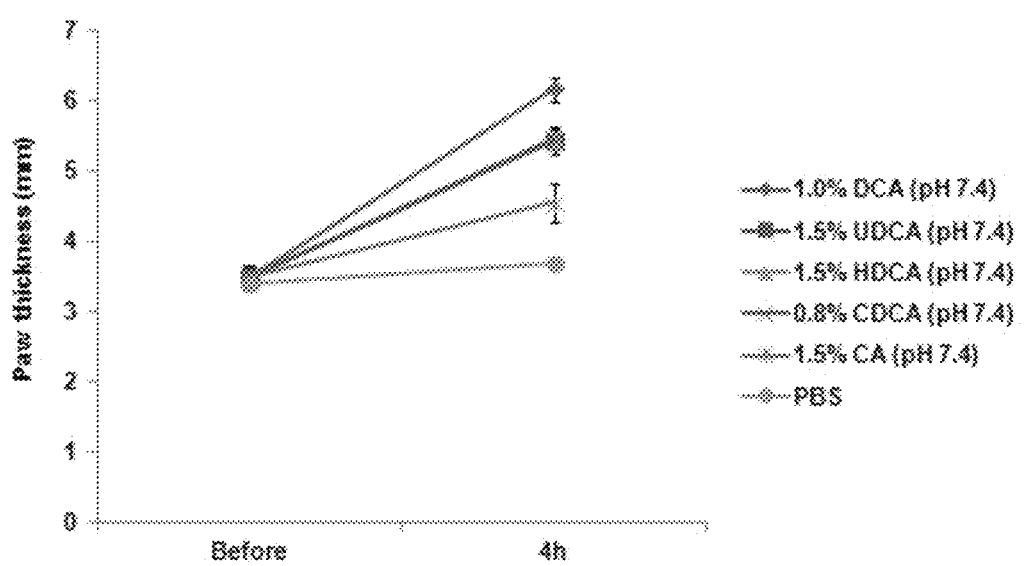
Figure 17E:
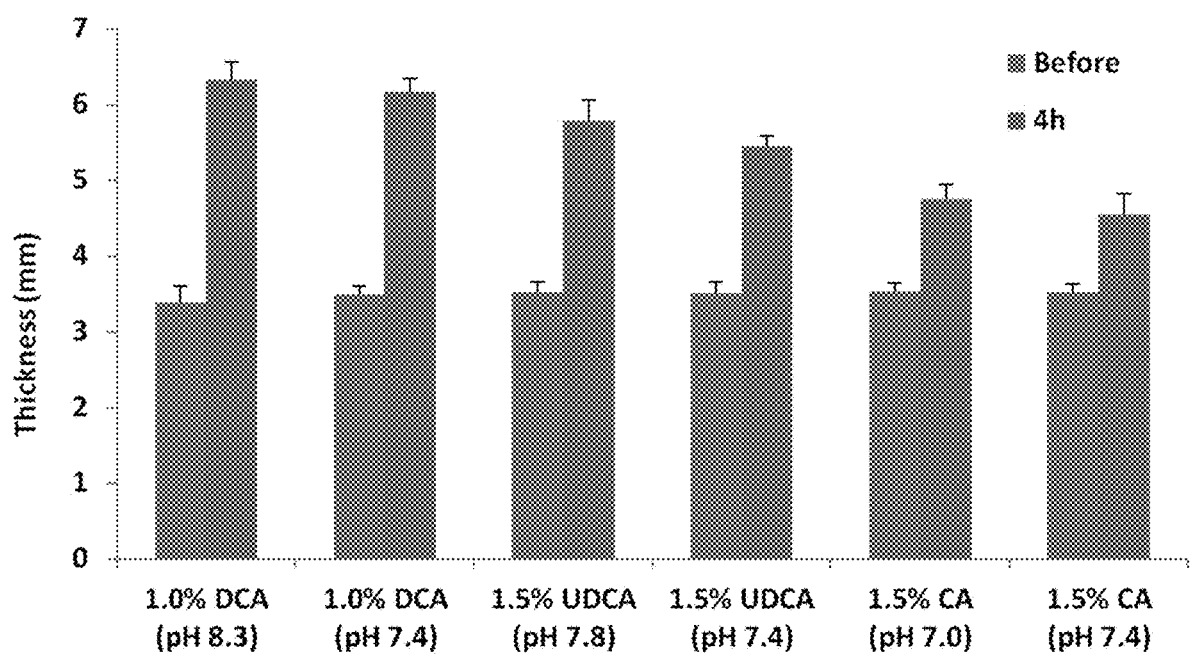

Edema is one of the typical adverse events caused by DCA injection. Severity of edema was monitored by thickness of rat paws after bile salts injection (FIGS. 17A, 17B, 17C, 17D, and 17E). Formulation of bile salt solutions were adjusted as concentrations and pHs showing similar tissue lysis effects (FIGS. 17A and 17B). Injection of same volume of PBS showed no increment of paw thickness. In contrast, injection of bile salts increased the thickness of rat paws. Although tissue necrotic activities were similar in all bile salts compositions, severity of edema were differ in each bile salt. DCA administered paws showed most severe edema phenotype. UDCA, HDCA and CDCA showed slightly lower symptom after injection as compared with DCA. Most strikingly, swelling induced by CA injection was very mild as compared with DCA. Increment of foot thickness by CA was less than one-half of the case of DCA. These results were reproduced by the treatment of bile salts solutions having same pH (pH 7.4) (FIGS. 17C and 17D). Almost identical result with previous experiment indicates pH is not a factor affecting edema after bile acid injection (FIG. 17E).

Figures 18A, 18B:
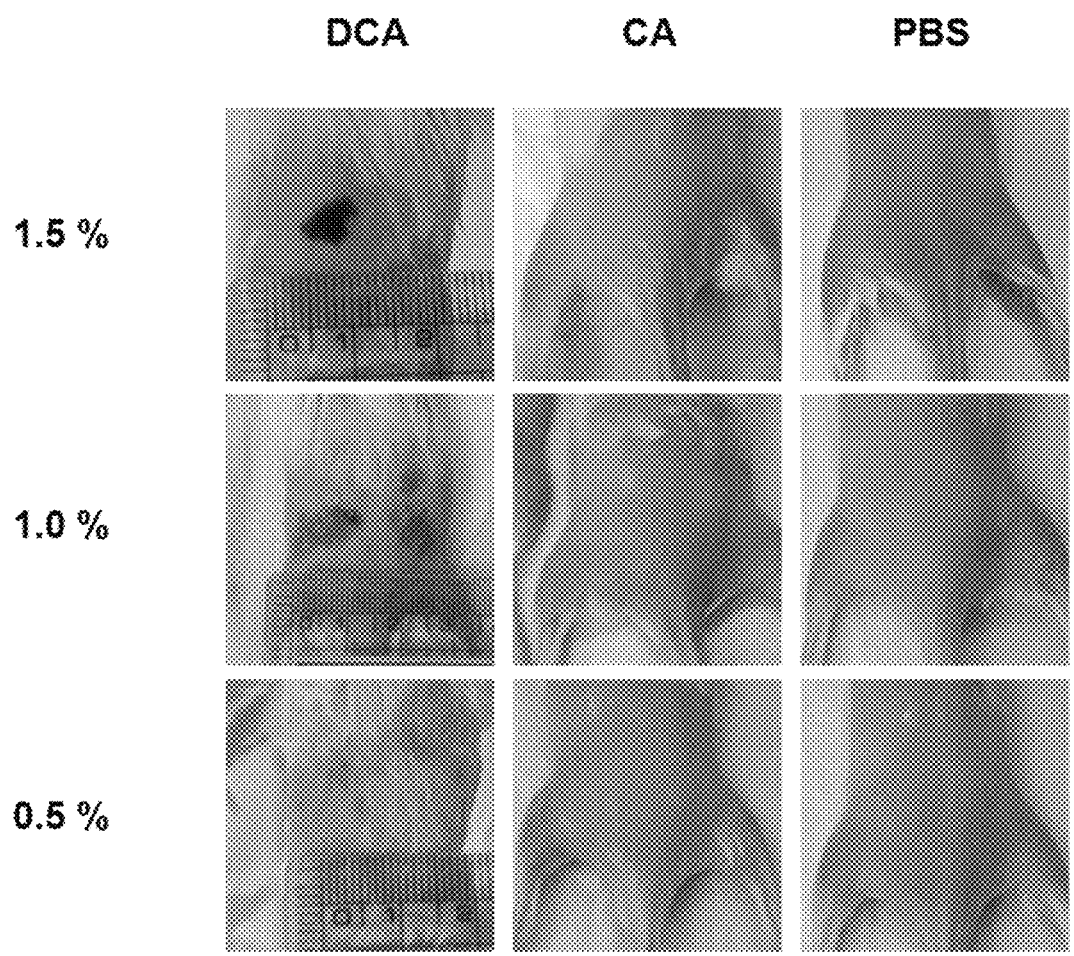
FIGS. 18A and 18B are images showing appearances of mice skin (FIG. 18A) and severities of skin lesions (FIG. 18B) after the subcutaneous injections of various concentrations (0.5-1.5%; in a pH 7.4 solution) of DCA, CA and PBS.

Next, the adverse effect of bile salt in the layer of skin was tested. Various concentrations of bile salts (adjusted to pH 7.4) and PBS were injected under the skin of live mice and the skin was monitored for any observed damage (FIGS. 18A and 18B). In the skin of PBS treated mice, no detectable lesions were founded. Treatment with DCA caused severe skin lesions on the injected area. Even treatment at the lowest dose (0.5%) of DCA induced small punctate lesions on the skin. Large lesions, erosions and ulcers were founded in the site of higher concentrations DCA injections. In contrast to DCA, injection with CA formed significantly less lesions on the injected area. Only small punctate lesions were observed in the higher dose of CA (1.5%). In lower doses, no detectable lesions were founded in the skin of CA treated mice. The damage of skin was scored by size and severity of lesions formed on the injection site of bile salts. Even the treatment of the highest dose of CA (1.5%) showed lower damage score compared to the treatment of the lowest dose of DCA (0.5%). These results indicate that the treatment of CA caused significantly reduced adverse events in the skin compared to the treatment of DCA.

Interestingly, only commercially available ingredient of lipolysis injection, DCA showed instability in physiological pH and had more severe adverse events after injection as compared to other bile salts. Among the tested bile salts, TUDCA did not have cell lysis activities in in vitro test and was excluded from further analysis. Although UDCA and CDCA had mild cell lytic activities in in vitro and ex vivo tests, they failed to show proper tissue lytic activities in in vivo tests. These compounds also showed that severe inflammation in injected sites. As a result, CDCA and CA were selected as proper ingredients for the lipolysis injection among these tested bile salts. Summary of these experiments is presented in Table 4.

TABLE 4

Properties of bile salts tested in this study

|  | DCA | CDCA | UDCA | HDCA | TUDCA | CA |
|---|---|---|---|---|---|---|
| In vitro cell lysis effect | +++ | +++ | + | ++ | − | +/− |
| Ex vivo cell lysis effect | +++ | +++ | n.d.* | ++ | n.d.* | + |
| In vivo cell lysis effect | +++ | +++ | + | + | n.d.* | ++ |
| pH stability | <8.3 | <7.4 | <7.8 | <7.4 | n.d.* | <7.0 |
| Inflammation of injection site | +/− | +/− | +++ | +++ | n.d.* | +/− |
| Adverse event: edema | +++ | ++ | ++ | ++ | n.d.* | + |
| Adverse event: skin | +++ | ++ | + | + | n.d.* | + |

*n.d.: not determined

The results presented herein are believed to be the first study that evaluates the efficacy of fat lysis by individual bile salts. Although the strength of a detergent is a critical determinant of the fat lysis effects of bile salts, different dosage responses of CA in in vitro, ex vivo and in vivo conditions suggest that lysis effects of individual bile salts can be modulated by their environments. Unexpected high lysis activity in vivo and reduced adverse event on injected area of CA facilitates the development of a safer lipolysis injection.

The results presented herein demonstrate that in lower pH, such as those used in the experiments disclosed herein, a lower concentration of bile salts can be used because a lower pH can enhance the cell lysis activity of the bile salt. However, the lower pH used in the present experiments did not increase the adverse effects of the bile salt formulation. These results demonstrate that the adverse effects can be distinguished from the cell lytic activity in a proper pH condition. Therefore, the use of a lower concentration and a lower pH of bile salts can reduce the adverse effects without reduction of cell lytic activity. Moreover, neutral pH can reduce the adverse effect associated with injection pain.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A formulation comprising about 0.5% to about 4% cholate by weight, and at least one pharmaceutically acceptable carrier, wherein the formulation has a pH of about 8 or less, and the formulation is an aqueous solution and is free of precipitate or gel form at 25° C.

2. The formulation of claim 1, wherein the formulation has a pH of about 7.5 or less.

3. The formulation of claim 1, wherein the formulation has a pH of about 7 to about 8.

4. The formulation of claim 3, wherein the formulation has a pH of about 7 to about 7.5.

5. The formulation of claim 3, wherein the formulation has a pH of about 7.5 to about 8.

6. The formulation of claim 1, wherein the formulation has cholate from about 0.5% by weight to about 2.0% by weight.

7. The formulation of claim 1, wherein at least one pharmaceutically acceptable carrier is selected from the group consisting of an excipient; a surface active agent; a dispersing agent; an inert diluent; a granulating and disintegrating agent; a binding agent; a lubricating agent; a sweetening agent; a flavoring agent; a coloring agent; a preservative; an aqueous vehicle and solvent; an oily vehicle and solvent; a suspending agent; a wetting agent; an emulsifying agent; a demulcent; a buffer; a salt; a thickening agent; a filler; an antioxidant; an antibiotic; an antifungal agent; and a stabilizing agent.

8. The formulation of claim 7, wherein the formulation comprises a buffer.

9. The formulation of claim 7, wherein the formulation comprises an emulsifying agent.

10. The formulation of claim 1, further comprising a therapeutic agent selected from the group consisting of an anti-microbial agent, a vasoconstrictor, an anti-thrombotic agent, an anti-coagulation agent, a suds-depressant, an anti-inflammatory agent, an analgesic, an anti-dispersion agent, a penetration enhancer, a steroid, a tranquilizer, a muscle relaxant, an anti-diarrhea agent, and any combination thereof.

11. The formulation of claim 1, wherein the formulation is an injectable formulation.

12. The formulation of claim 1, wherein the formulation is a lipolysis injection formulation.

13. The formulation of claim 1, wherein the formulation is suitable for subcutaneous injection.

* * * * *